United States Patent [19]
Parker et al.

[11] Patent Number: 6,114,572
[45] Date of Patent: Sep. 5, 2000

[54] SUBSTITUTED PHENOLS AND THIOPHENOLS USEFUL AS ANTIOXIDANT AGENTS

[75] Inventors: Roger A. Parker; Paul S. Wright, both of Cincinnati, Ohio; Steven J. Busch, Stewartsville, N.J.; Kim S. Chen, San Diego, Calif.; Mark T. Yates, Ann Arbor, Mich.

[73] Assignee: Hoechst Marion Roussel, Inc., Bridgewater, N.J.

[21] Appl. No.: 08/974,112

[22] Filed: Nov. 19, 1997

Related U.S. Application Data

[60] Provisional application No. 60/092,110, Nov. 20, 1996.

[51] Int. Cl.⁷ .......................... C07C 67/02; C07C 59/00; C07C 41/00; A01N 31/00

[52] U.S. Cl. .......................... 560/254; 560/130; 560/135; 560/144; 568/39; 568/630; 568/784; 514/713; 514/720; 514/824; 514/826; 514/886; 514/885

[58] Field of Search .................................... 560/254, 130, 560/135, 144; 568/39, 630, 784; 514/713, 720, 824, 826, 886, 885

[56] References Cited

U.S. PATENT DOCUMENTS

| | | |
|---|---|---|
| 3,129,262 | 4/1964 | Laufer . |
| 3,246,039 | 4/1966 | Relfschneider . |
| 3,274,257 | 9/1966 | Relfschneider . |

(List continued on next page.)

FOREIGN PATENT DOCUMENTS

| | | |
|---|---|---|
| 9460533 | 10/1994 | Australia . |
| 2106687 | 9/1992 | Canada . |
| 0374048 | 12/1989 | European Pat. Off. . |
| 0372542 | 6/1990 | European Pat. Off. . |
| 0464844 | 1/1992 | European Pat. Off. . |
| 0464852 | 1/1992 | European Pat. Off. . |
| 0476493 | 3/1992 | European Pat. Off. . |
| 0505923 | 9/1992 | European Pat. Off. . |
| 0589069 | 3/1994 | European Pat. Off. . |
| 2308372 | 11/1976 | France . |
| 7330595 | 12/1995 | Japan . |
| 1199871 | 5/1968 | United Kingdom . |
| 1311577 | 3/1973 | United Kingdom . |
| 9312089 | 6/1993 | WIPO . |
| 9321914 | 11/1993 | WIPO . |
| 9405333 | 3/1994 | WIPO . |
| 9409772 | 5/1994 | WIPO . |
| 9411027 | 5/1994 | WIPO . |
| 9414786 | 7/1994 | WIPO . |
| 9416094 | 7/1994 | WIPO . |
| 9417828 | 8/1994 | WIPO . |
| 9504749 | 2/1995 | WIPO . |

OTHER PUBLICATIONS

Robillard et al, J of Organic Chem., vol. 51, No. 10, 1986, pp 1700–1704.

John et al, Berichte Der Deutschen Chemiscren Gesellschaft, vol. 73, No. 9 (Sep. 4, 1940) pp 995–1001.

Gaertner et al, J of the American Oil Chemist Society, vol. 38, (Apr./1961) pp 212–215.

(List continued on next page.)

Primary Examiner—Gary Geist
Assistant Examiner—Robert W. Deemie
Attorney, Agent, or Firm—Michael W. Ferrell

[57] ABSTRACT

The present invention provides compounds of the formula

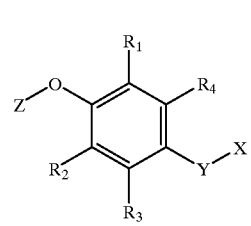

(1)

wherein

X is selected from the group consisting of

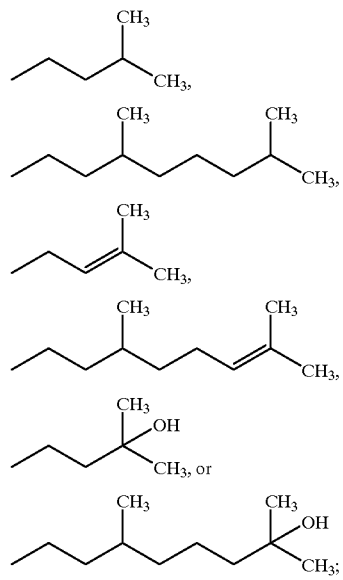

Y is thio, oxy or a methylene group;

Z is hydrogen or —C(O)—(CH$_2$)$_m$—Q wherein Q is hydrogen or —COOH and m is an integer 1, 2, 3 or 4;

R$_1$ is C$_1$–C$_6$ alkyl; and

R$_2$, R$_3$ and R$_4$ are each independently hydrogen or C$_1$–C$_6$ alkyl;

or a stereoisomer thereof; useful for the treatment of atherosclerosis and chronic inflammatory disorders; for inhibiting cytokine-induced expression of VCAM-1 and/or ICAM-1; for inhibiting the peroxidation of LDL lipid; for lowering plasma cholesterol; and as anti-oxidant chemical additives useful for preventing oxidative deterioration in organic materials.

32 Claims, No Drawings

U.S. PATENT DOCUMENTS

| | | |
|---|---|---|
| 3,303,209 | 2/1967 | Relfschneider . |
| 3,506,674 | 4/1970 | Berger . |
| 3,576,883 | 4/1971 | Neuworth . |
| 3,655,773 | 4/1972 | Relfschneider . |
| 3,751,483 | 8/1973 | Cisney et al. . |
| 3,786,100 | 1/1974 | Neuworth . |
| 3,801,617 | 4/1974 | Fletcher . |
| 3,839,586 | 10/1974 | Ludvik . |
| 3,853,776 | 12/1974 | Clark et al. . |
| 3,862,332 | 1/1975 | Barnhart et al. . |
| 3,897,500 | 7/1975 | Neuworth . |
| 4,379,783 | 4/1983 | Melvin et al. . |
| 4,388,404 | 6/1983 | Morigaki et al. . |
| 4,636,573 | 1/1987 | Pastor . |
| 4,663,314 | 5/1987 | Hayase et al. . |
| 4,670,421 | 6/1987 | DeVries et al. . |
| 4,719,237 | 1/1988 | McCaughan . |
| 4,734,527 | 3/1988 | Krauss . |
| 4,772,363 | 9/1988 | Van Effen . |
| 4,783,495 | 11/1988 | Pastor . |
| 4,861,443 | 8/1989 | Van Effen . |
| 4,870,101 | 9/1989 | Ku et al. . |
| 4,900,757 | 2/1990 | Mao et al. . |
| 4,904,653 | 2/1990 | Strunk et al. . |
| 4,975,467 | 12/1990 | Ku et al. . |
| 5,008,421 | 4/1991 | Brownell et al. . |
| 5,061,734 | 10/1991 | Mao et al. . |
| 5,112,870 | 5/1992 | Mao et al. . |
| 5,138,012 | 8/1992 | Riding et al. . |
| 5,155,250 | 10/1992 | Parker et al. . |
| 5,217,870 | 6/1993 | Hession et al. . |
| 5,272,263 | 12/1993 | Hession et al. . |
| 5,281,738 | 1/1994 | Parker et al. . |
| 5,304,668 | 4/1994 | Parker et al. . |
| 5,356,917 | 10/1994 | Panetta . |
| 5,367,056 | 11/1994 | Hession et al. . |
| 5,380,747 | 1/1995 | Medford et al. . |
| 5,393,887 | 2/1995 | Pearch . |
| 5,401,883 | 3/1995 | Laskovics et al. . |
| 5,574,178 | 11/1996 | Tamura et al. . |
| 5,606,089 | 2/1997 | Tamura et al. . |
| 5,663,373 | 9/1997 | Tamura et al. . |

OTHER PUBLICATIONS

Marui et al, American Society for Clinical Investigation, Inc. vol. 92, Oct., 1993, pp 1866–1874. Vascular Cell Adhesion Molecule–1.

Boschelli et al, J. Med. Chem. 1995, 38, pp 4597–4614. Inhibition of E–Selection–,ICAM–1–, and VCAM–1–.

Volin et al, FASEB Journal, Federation of American Societies for Experimental Biology, Mar. 10, 1995, vol.

Derwent Abstract, 94–322148/40 (B.17).

Derwent Abstract, 94–322152/40 (B.15).

Abstract 009, Pres. made at 211th ACS National Meeting, Mar. 24–28, 1996, Medicinal Chemical Divison, Ref. Bioorganic & Medicinal Chemistry Letter, vol. 6, pp 533–538, 1996.

Derwent Abstract, 94–325887/41 (B.11&12).

Alerting Bulletin 92–324750/49 Abbreviated Abstract for JP06505732–W (B.17).

Alerting Bulletin 92–332847/41 Abbreviated Abstract for JP06505735–W (B.13).

Parthasarathy, et al, "Probucol inhibits oxidative modification of low density lipoprotein", J. Clin. Invest., Vo.

Product Labeling for Lorelco, Physician's Desk Reference, 42nd edition, (1988), Medical Economics Co., Inc., Oradell, N.J.

Gotteland et al, J. Med. Chem., 1995, 38, pp 3207–3216.

ilewski et al, Am. J.Respir. Cell Mol. Biol. vol. 12, pp 1–3, 1995.

Steinberg, "Studies on the Mechanism of Action of Probucol", The American Journal of Cardiology, vol. 57, pp 16H–21H.

Satonin et al, "Comparison of gas chromatography and high–performance liquid chromatography for the analysis of probucol in plasma" Journal of Chromatography, 380 (1986) pp 401–406.

Mao et al, "Monoclonal Antibodies to human . . . I", Clinical Chemistry, vol. 29, No. 11, 1983, pp 1890–1897.

Mao et al, "Monoclonal Antibodies to human . . . II", Clinical Chemistry, vol. 29, No. 11, 1983 pp 1898–1903.

Miller, "High Density Lipoproteins and Atherosclerosis", Ann. Rev. Med. 1980 31:97–108.

Brown et al, Lipoprotein Metabolism in the Macrophage: Implications for Cholesterol Deposition in Atheros.

Maciejko et al, "Apolipoprotein A–1 as a marker of angiographically assessed coronary–artery disease", The New England Journal of Medicine, 309:385–389 (Aug. 18, 1983).

Mao et al, "Immunochemistry oif human plasma high density lipoproteins . . . " Biochemistry, 1975, 14, pp 4127.

Badimon et al, "Quantification and immunolocalization of apolipoprotein E . . . ", Atherosclerosis, 61 (1986) 57–66.

Mao et al, "Immunochemistry of human plasma high density lipoproteins . . . ", Biochemistry, vol. 14, No. 18, 1975, pp 4127–4131.

Kita et al, "Probucol prevents the priogression of atherosclerosis in Watanabe heritable . . . " Medical Sciences, vol. 84, pp. 5928–5931, Aug. 1987.

Carew et al, "Antiatherogenic effect of probucol unrelated to its hypocholesterolemic effect . . . " Medical Sciences, vol. 84, pp 7725–7729, Nov., 1987.

Physician's Desk Reference, 44th edition, 1990, Medical Economics Co., Inc., Oradell, New Jersey.

Chemical Abstracts, vol. 108 (1988), 16125d: Proc. Natl. Acad. Sci. USA. 1987, 84(21), 7725–9.

S.J.T. Mao, et al., J. of Medicinal Chemistry 34, 298–302 (1991). From Mao.

S.J.T. Mao et al., Arteriosclerosis and Thrombosis, vol. 11, No. 5, pp. 1266–1275 (1991) From Mao.

R.L. Jackson et al., Hypercholesterolemia, Hypocholesterolemia, Hypertriglyceridemia, Plenum Press, NY pp 367–372 (1990) From Mao.

J. L. Witztum, Hypercholesterolemia, Hypocholesterolemia, Hypertriglyceridemia, Plenum Press, NY pp 353–365 (1990) From Mao.

M. Aviram, Artherosclerosis 98 (1993) 1–9. From Mao.

S.R. Srinivasan et al., Hypercholesterolemia, Hypocholesterolemia, Hypertriglyceridemia, Plenum Press, NY pp 373–381 (1990) From Mao.

Chemical abstracts online printout; 66:65162, rn = 13537–63–8, Kheifits et al.

SUBSTITUTED PHENOLS AND THIOPHENOLS USEFUL AS ANTIOXIDANT AGENTS

This application claims the benefit of Provisional Application No. 60/092,110, filed Nov. 20, 1996, which was converted from application Ser. No. 08/755,528, filed Nov. 20, 1996.

BACKGROUND OF THE INVENTION

Coronary heart disease (CHD) remains a leading cause of death in the industrialized countries. Despite recent declines in CHD mortality, CHD is still responsible for more than 500,000 deaths in the U.S. annually. It is estimated that CHD, directly and indirectly, costs the U.S. more than $100 billion a year. The primary cause of CHD is atherosclerosis, a disease characterized by the deposition of lipids in the arterial vessel wall, resulting in a narrowing of the vessel passages and ultimately hardening the vascular system.

Atherosclerosis as manifested in its major clinical complication, ischaemic heart disease, is thought to begin with local injury to the arterial endothelium followed by proliferation of arterial smooth muscle cells from the medial layer to the intimal layer along with deposition of lipid and accumulation of foam cells in the lesion. As the atherosclerotic plaque develops, it progressively occludes more and more blood vessel and can eventually lead to ischaemia or infarction. Therefore, it is desirable to provide a method of inhibiting the progression of atherosclerosis in patients in need thereof.

Hypercholesterolemia is an important risk factor associated with CHD. For example, in December 1984, a National Institute of Health Consensus Development Conference Panel concluded that lowering plasma cholesterol levels (specifically blood levels of low-density lipoprotein cholesterol) will definitely reduce the risk of heart attacks due to CHD. Serum lipoproteins are the carriers for lipids in the circulation. They are classified according to their density: chylomicrons, very low-density lipoproteins (VLDL), low density lipoproteins (LDL) and high-density lipoproteins (HDL). Chylomicrons mainly participate in transporting dietary triglycerides and cholesterol from the intestine to adipose tissue and liver. VLDL deliver endogenously synthesized triglycerides from liver to adipose and other tissues. LDL transports cholesterol to peripheral tissues and regulate endogenous cholesterol levels in those tissues. HDL transports cholesterol from peripheral tissues to the liver. Arterial wall cholesterol is derived almost exclusively from LDL. Brown and Goldstein, *Ann. Rev. Biochem.* 52, 223 (1983); Miller, *Ann. Rev. Med.* 31, 97 (1980)). In patients with low levels of LDL, the development of atherosclerosis is rare. Accordingly, it is desirable to provide a method for reducing plasma cholesterol in patients with hypercholesterolemia or at risk of developing hypercholesterolemia.

Elevated cholesterol levels are also associated with a number of disease states, including restenosis, angina, cerebral arteriosclerosis, and xanthoma. It is desirable to provide a method for reducing plasma cholesterol in patients with, or at risk of developing, restenosis, angina, cerebral arteriosclerosis, xanthoma, and other disease states associated with elevated cholesterol levels.

Vascular cell adhesion molecule-1 (VCAM-1) and intercellular adhesion molecule-1 (ICAM-1) are adhesion molecules in the immunoglobulin superfamily that are upregulated in vascular endothelial and smooth muscle cells by cytokines, such as, for example, interleukin-1 (IL-1), interleukin-4 (IL-4) and tumor necrosis factor-$\alpha$ (TNF-$\alpha$). Through interaction with the appropriate integrin counter receptor, VCAM-1 and ICAM-1 mediate adhesion and transendothelial migration of leukocytes in inflammatory responses. Inhibitors of VCAM-1 and/or ICAM-1 have therapeutic applications for many types of chronic inflammatory disorders including atherosclerosis, asthma, rheumatoid arthritis, and autoimmune diabetes. For example, in situ hybridization and immunohistochemical analysis of atherosclerotic plaques from patients demonstrate an increased level of adhesion molecules (VCAM-1 and ICAM-1) when compared with non-disease areas. O'Brien, K. D. et al., *J. Clin. Invest.* 92, 945–951 (1993); Davies, M. J. et al., *J. Pathol.* 171, 223–229 (1993); Poston, R. N. et al., *Am. J. Pathol.* 140, 665–673 (1992). An atherogenic diet induces VCAM-1 expression in rabbit aortic endothelium and vascular smooth muscle cells within atheromas. Poston, R. N. et al., Ibid.; Cybulsky, M. I. et al., *Science* 251, 788–791 (1991); Li, H. et al., *Arterioscler. Thromb.* 13, 197–204 (1993). Considering these previous studies, increased VCAM-1 expression is believed to be associated with initiation and progression of atherosclerotic plaques through recruitment of circulating monocytes to the lesion area.

Furthermore, VCAM-1 is also involved as a mediator in other chronic inflammatory disorders such as asthma, rheumatoid arthritis and autoimmune diabetes. For example, it is known that the expression of VCAM-1 and ICAM-1 are increased in asthmatics. Pilewski, J. M. et al., *Am. J. Respir. Cell Mol. Biol.* 12, 1–3 (1995); Ohkawara, Y. et al., *Am. J. Respir. Cell Mol. Biol.* 12, 4–12 (1995). Additionally, blocking the integrin receptors for VCAM-1 and ICAM-1 (VLA-4 and LFA-1, respectively) suppressed both early and late phase responses in an ovalbumin-sensitized rat model of allergic airway responses. Rabb, H. A. et al., *Am. J. Respir. Care Med.* 149, 1186–1191 (1994). There is also increased expression of endothelial adhesion molecules, including VCAM-1, in the microvasculature of rheumatoid synovium. Koch, A. E. et al, *Lab. Invest.* 64, 313–322 (1991); Morales-Ducret, J. et al., *Immunol.* 149, 1421–1431 (1992). Neutralizing antibodies directed against VCAM-1 or its counter receptor, VLA-4, can delay the onset of diabetes in a mouse model (NOD mice) which spontaneously develop the disease. Yang, X. D. et al., *Proc. Natl. Acad. Sci. USA* 90, 10494–10498 (1993); Burkly, L. C. et al., *Diabetes* 43, 523–534 (1994); Baron, J. L. et al., *J. Clin. Invest.* 93, 1700–1708 (1994). Monoclonal antibodies to VCAM-1 can also have a beneficial effect in animal models of allograft rejection, suggesting that inhibitors of VCAM-1 expression may have utility in preventing transplant rejection. Orocz, C. G. et al., *Immunol. Lett.* 32, 7–12 (1992).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea. Koch, A. E. et al., *Nature* 376, 517–519 (1995). Inhibitors of the expression of soluble VCAM-1 have potential therapeutic value in treating diseases with a strong angiogenic component, including tumor growth and metastasis. Folkman, J., and Shing, Y., *J. Biol. Chem.* 10931–10934 (1992).

The promoters for both VCAM-1 and ICAM-1 have been cloned and characterized. For example, both promoters contain multiple DNA sequence elements which can bind the transcription factor, NF-kB. Iademarco, M. F. et al., *J. Biol. Chem.* 267, 16323–16329 (1992); Voraberger, G. et al., *J. Immunol.* 147, 2777–2786 (1991). The NF-kB family of transcription factors is central in the regulation of several genes upregulated within sites of inflammation. The activation of NF-kB as a transcription factor involves dissociation from an inhibitory subunit, IkB, in the cytoplasm. NF-kB subunits translocate to the nucleus, bind to specific DNA sequence elements, and activate transcription of several genes, including VCAM-1 and ICAM-1. Collins T. et al., *Lab. Invest.* 68, 499–508 (1993).

It has been postulated that regulation of VCAM-1 gene expression may be coupled to oxidative stress through specific reduction-oxidation (redox) sensitive transcriptional or posttranscriptional regulatory factors. The antioxidants pyrollidine dithiocarbamate and N-acetylcysteine inhibit cytokine-induced expression of VCAM-1, but not ICAM-1 in vascular endothelial cells. Mauri, N. et al., *J. Clin. Invest.* 92, 1866–1874 (1993). This would indicate that the inhibition of VCAM-1 expression by antioxidants involves some additional factors not involved in the regulation of ICAM-1 expression.

2,6-Di-alkyl-4-silyl-phenols are disclosed as antiatherosclerotic agents by Parker et al. in U.S. Pat. No. 5,155,250, issued Oct. 13, 1992. Furthermore, 2,6-Di-alkyl-4-silyl-phenols are disclosed as serum cholesterol lowering agents in PCT International Publ. No. WO 95/15760, published Jun. 15, 1995.

It would be advantageous to control the release of VCAM-1 and/or ICAM-1, and to treat VCAM-1 and/or ICAM-1 mediated effects. It would also be advantageous to control or treat chronic inflammation, without production of concomitant side effects known to accompany the use of antiinflammatory steroids and non-steroidal antiinflammatory agents.

SUMMARY OF THE INVENTION

The present invention provides compounds of the formula (1)

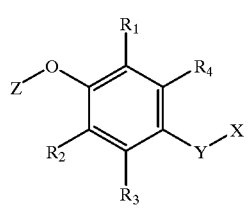

wherein

X is selected from the group consisting of

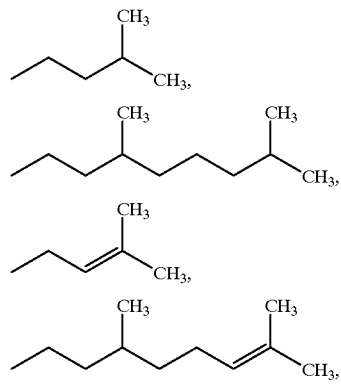

-continued

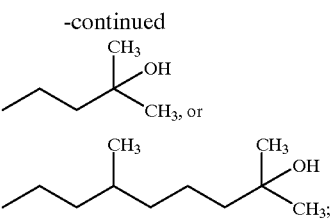

Y is thio, oxy or a methylene group;

Z is hydrogen or —C(O)—(CH$_2$)$_m$—Q wherein Q is hydrogen or —COOH and m is an integer 1, 2, 3 or 4;

R$_1$ is C$_1$–C$_6$ alkyl; and

R$_2$, R$_3$ and R$_4$ are each independently hydrogen or C$_1$–C$_6$ alkyl;

or a stereoisomer thereof.

The present invention also provides a method of inhibiting the peroxidation of LDL lipid in a patient in need thereof comprising administering to said patient an effective antioxidant amount of a compound of formula (1).

The present invention further provides a method for lowering plasma cholesterol level in a patient in need thereof by administration of a plasma cholesterol lowering amount of a compound of formula (1).

The present invention further provides a method for inhibiting the progression of atherosclerosis and/or a method for treating atherosclerosis in a patient in need thereof comprising administering to the patient an antiatherosclerotic amount of a compound of formula (1).

The present invention further provides a method of inhibiting cytokine-induced expression of vascular cell adhesion molecule-1 and/or intercellular adhesion molecule-1 in a patient in need thereof comprising administering to the patient an effective vascular cell adhesion molecule-1 and/or intercellular adhesion molecule-1 inhibiting amount of a compound of formula (1).

The present invention further provides a method of treating a patient afflicted with a chronic inflammatory disease comprising administering to the patient a therapeutically effective amount of a compound of formula (1).

DETAILED DESCRIPTION OF THE INVENTION

As used in this application:

a) the designation "▶—" refers to a bond that protrudes forward out of the plane of the page;

b) the designation "⊪—" refers to a bond that protrudes backward out of the plane of the page;

c) the designation "—" refers to a bond between achiral molecules or a bond between chiral molecules for which the stereochemistry is not designated.

As used herein, the term "C$_1$–C$_6$ alkyl" refers to a saturated hydrocarbyl radical of straight, branched or cyclic configuration made up of from one to six carbon atoms. Included within the scope of this term are methyl, ethyl, n-propyl, isopropyl, n-butyl, isobutyl, sec-butyl, tertiarybutyl, n-pentyl, n-hexyl, cyclohexyl and the like.

The term "stereoisomers" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereomers).

The compounds of formula (1) can be prepared by utilizing procedures and techniques well known and appreciated by one of ordinary skill in the art. A general synthetic scheme for preparing compounds of formula (1) is set forth in Scheme A, wherein all substituents, unless otherwise indicated, are previously defined.

SCHEME A

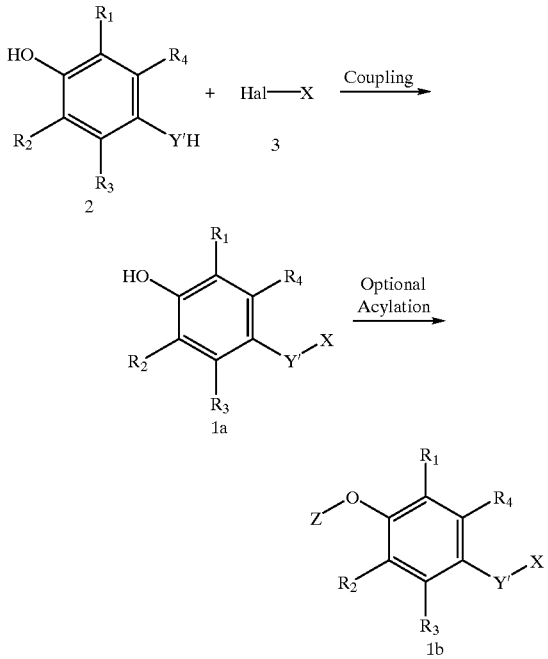

Y' = S or O
Hal = chlorine, bromine or iodine

In general, a phenol of structure 1a can be prepared by reacting the appropriate alkyl-4-mercaptophenol or alkylhydroquinone of structure 2 (or suitably protected derivatives) with a non-nucleophilic base, such as sodium hydride, potassium carbonate, cesium carbonate, sodium hydroxide, potassium hydroxide, and the like, and the appropriate haloalkane or haloalkene of structure 3, such as the appropriate bromoalkane, in a suitable aprotic solvent, such as acetonitrile, dimethylformamide or dimethylacetamide, or in an aqueous solvent, such as water/2-butanone.

A phenol ester of structure 1b can be prepared by acylating a phenol of structure 1a according to standard acylation techniques. For example, a phenol of structure 1a is dissolved in a suitable aprotic solvent such as acetonitrile, dimethylformamide or dimethylacetamide, or an ethereal solvent such as diethyl ether or dioxane, and treated with a suitable base, such as triethylamine, N-methylmorpholine, sodium hydroxide or sodium hydride. An excess of O-acylating agent is then added at room temperature and the reaction is stirred at room temperature for 1 to 24 hours. Examples of O-acylating agents are acetyl chloride, propionyl chloride, monoethylsuccinyl-chloride, succinic anhydride, and the like. The product is then purified by techniques well known in the art, such as extractive methods and flash chromatography. Optionally, additional treatment with a suitable base, such as sodium hydroxide with subsequent acidification with a suitable acid, such as hydrochloric acid, followed by extraction and flash chromatography may be performed to provide the phenol ester of structure 1b.

Starting materials for use in the general synthetic procedure outlined in Scheme A are readily available to one of ordinary skill in the art. For example, certain phenol starting materials for various compounds of formula (1) wherein Z is sulfur, such as 2,6-di-tertiarybutyl-4-mercaptophenol and 2-tertiarybutyl-4-mercaptophenol are described in the following patents: U.S. Pat. No. 3,576,883, U.S. Pat. No. 3,952,064, U.S. Pat. No. 3,479,407, U.S. Pat. No. 4,975,467, U.S. Pat. No. 5,155,250 and in Japanese Patent Application 73-28425. Other phenol starting materials for compounds of formula (1) include trimethylhydroquinone, tertiarybutyl-1,4-hydroquinone, and 2,5-di-tertiarybutylhydroquinone which are commercially available.

The haloalkane and haloalkene starting materials of structure 3, such as (R)-(−)-citronellyl bromide, (S)-(+)-citronellyl bromide, 1-bromo-3,7-dimethyloctane, 1-bromo-3-methylbutane, and 4-bromo-2-methyl-2-butene are commercially available.

In the special instance where X is the moiety of the formulae:

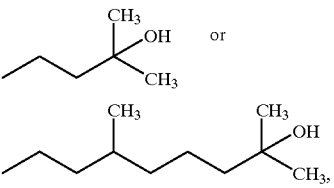

an appropriate intermediate of structure 3 as represented by the formulae (3a) or (3b)

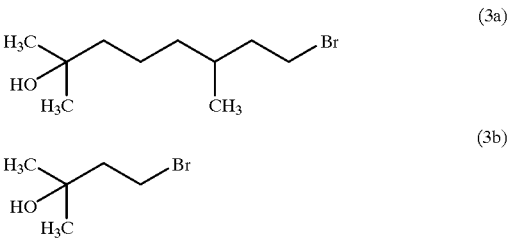

is prepared by adding methanesulfonyl chloride to a mixture of 3-methyl-1,3-butanediol or hydroxycitronellol, lithium bromide, 2,4,6-collidine and dimethylformamide, while stirring at room temperature. The mixture is stirred for several days, diluted with water and ether and extracted by techniques well known in the art to provide an intermediate of structure (3a) or (3b).

In those instances where the 1-phenol functionality of a compound of structure 2 may react with the compounds of structure 3 under the conditions of the reaction, the 1-phenol functionality of compound of structure 2 may be blocked with standard phenol blocking agents which are well known and appreciated in the art. The selection and utilization of particular blocking groups are well known to one of ordinary skill in the art. In general, blocking groups should be selected which adequately protect the phenol in question during subsequent synthetic steps and which are readily removable under conditions which will not cause degradation of the desired product.

Examples of suitable phenol protecting groups are ethers, such as methoxymethyl, 2-methoxyethoxymethyl, tetrahydro-pyranyl, t-butyl and benzyl; silyl ethers, such as trimethylsilyl and t-butyldimethylsilyl; esters, such as acetate and benzoate; carbonates, such as methylcarbonate and benzylcarbonate; as well as sulfonates, such as methanesulfonate and toluenesulfonate.

In those instances where $R_1$ and $R_2$ are each t-butyl, the reaction of Scheme A may be conveniently carried out without blocking of the 1-phenol functionality.

The following examples present typical syntheses as described in Scheme A. These examples are understood to be illustrative only and are not intended to limit the scope of the present invention in any way. As used herein, the following terms have the indicated meanings: "g" refers to grams; "mol" refers to moles; "mmol" refers to millimoles; "L" refers to liters; "mL" refers to milliliters; "bp" refers to boiling point; "°C." refers to degrees Celsius; "mm Hg" refers to millimeters of mercury; "mp" refers to melting point; "mg" refers to milligrams; "$\mu$M" refers to micromolar; "$\mu$g" refers to micrograms; "h" or "hrs." refers to hours, "min" refers to minutes.

EXAMPLE 1

Phenol, 2,6-bis(1,1-dimethylethyl)-4-[(3,7-dimethyl-6-octenyl)oxy]-, (S)- (MDL 103,294)

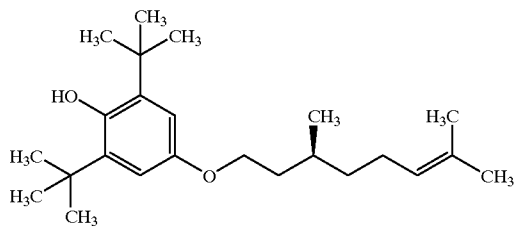

Mix 2,6-di-t-butyl-1,4-hydroquinone (9.0 g, 40.5 mmol), potassium carbonate (5.6 g), S-(+)-citronellyl bromide (8.9 g, 40.5 mmol, Aldrich), and acetonitrile (150 mL, degassed under argon), heat to reflux and stir for four days under argon atmosphere. Cool dilute the mixture with water and extract with diethyl ether. Wash the ether layer with water and evaporate to dryness to give an oil (14.5 g). Distill the oil in a kugelrohr. Starting material (2.5 g, 130° C., 0.1 mm Hg) may be collected prior to collection of other fractions. An additional fraction collected (140–165° C., 0.1 mm Hg) gives an oil (11.7 g) which is followed by chromatography on silica gel (chloroform). Redistillation on a kugelrohr (135–150° C., 0.1 mm Hg) gives a light yellow oil (11.4 g).

Anal. Calcd. for $C_{24}H_{40}O_2$: C, 79.94; H, 11.18 Found: C, 80.55; H, 11.17.

EXAMPLE 2

Phenol, 2-(1,1-dimethylethyl)-4-[(3,7-dimethyl-6-octenyl)oxy]-, (S)- (MDL 103,649)

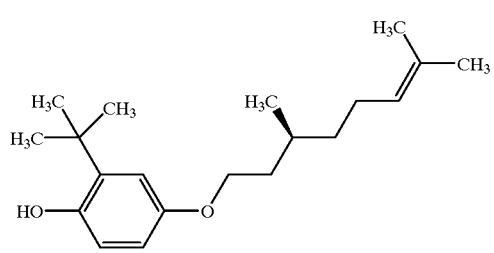

Mix t-butyl-1,4-hydroquinone (4.2 g, 25.8 mmol, Aldrich), potassium carbonate (3.5 g), S-(+)-citronellyl bromide (5.5 g, 25.1 mmol), and acetonitrile (150 mL, degassed under argon), heat to reflux and stir for four days under argon atmosphere. Cool dilute the mixture with water and extract with diethyl ether. Wash the ether layer with water and evaporate to dryness to give an oil (7.9 g). Distill the oil in a kugelrohr. Starting material (1.6 g, to 120° C., 0.1 mm Hg) may be collected prior to collection of other fractions. An additional fraction collected (140–165° C., 0.1 mm Hg) gives an oil (5.8 g) which is followed by chromatography on silica gel (chloroform). The oil is redistilled on a kugelrohr (138–170° C., 0.1 mm Hg) followed by chromatography on silica gel (hexane-$CH_2Cl_2$ 3:1–1:1). Redistill the resulting product on a kugelrohr (140–150° C., 0.1 mm Hg) and redistill a final time (138–150° C., 0.1 mm Hg) to give the title compound (4.0 g).

Anal. Calcd. for $C_{20}H_{32}O_2$: C, 78.89; H, 10.60 Found: C, 79.51; H, 10.44.

EXAMPLE 3

Phenol, 2-(1,1-dimethylethyl)-4-[(3,7-dimethyl-6-octenyl)thio]-, (S)- (MDL 103,714)

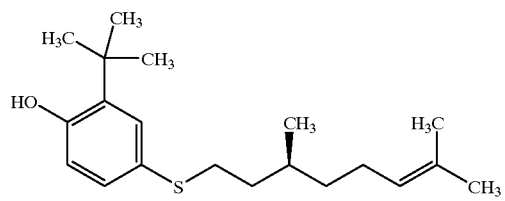

Mix 2-t-butyl-4-mercaptophenol (8.0 g, 44 mmol), potassium bicarbonate (4.4 g, 44 mmol), potassium carbonate (0.1 g), S-(+)-citronellyl bromide (9.6 g, 44 mmol), and isopropanol (150 mL, degassed under argon), heat to reflux and stir for about 0.5 hrs. under argon atmosphere. Distill off the azeotrope of $H_2O$.isopropanol and continue to reflux the mixture overnight for about 24 hrs. Remove the solvent by distillation (steam bath). Dilute the residue with $H_2O$, acidify with conc. hydrochloric acid and extract with diethyl ether. Wash the ether layer with water and brine and evaporate to dryness give an oil (16.2 g). Distill the oil in a kugelrohr. Starting material (3.5 g, 120° C., 0.25–0.1 mm Hg) may be collected prior to collection of other fractions. An additional fraction collected (130–140° C., 0.1 mm Hg) gives an oil (9.7 g) which is redistilled (135–160° C., 0.1 mm Hg) to provide a colorless oil (9.4 g).

Anal. Calcd. for $C_{20}H_{32}OS$: C, 74.94; H, 10.06; S, 10.01 Found: C, 75.40; H, 10.19.

EXAMPLE 4

Phenol, 2,6-bis(1,1-dimethylethyl)-4-[(3,7-dimethyl-6-octenyl)thio]-, (MDL 103,960)

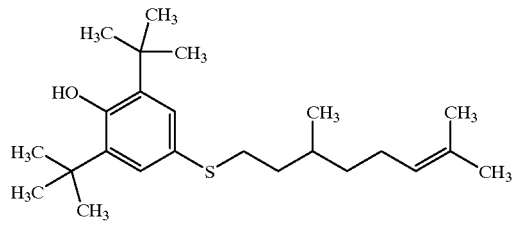

Stir a mixture of 2,6-di-t-butyl-4-mercaptophenol (10.0 g, 41.9 mmol), R-(−)-citronellyl bromide (9.2 g, 8.3 mL, 41.9 mmol) and isopropanol (150 mL, degassed under argon) at room temperature under positive argon. Add potassium bicarbonate (4.2 g, 41.9 mmol) and reflux the mixture with stirring overnight. Allow the isopropanol to distill off, add acetonitrile (~100 mL), reflux the reaction mixture for about 1 hr and allow the acetonitrile to distill off. Dilute the reaction mixture with water, acidify with conc. hydrochloric acid and extract with diethyl ether. Wash the ether layer with water and brine, filter through silica gel/$Na_2SO_4$ and evaporate to dryness give a light yellow oil (16.2 g). Distill the oil in a kugelrohr. A yellow oil fraction (1.6 g, 120° C., 0.25–0.1 mm Hg) may be collected prior to collection of other fractions. An additional fraction collected (140–165° C., 0.1 mm Hg) gives a colorless oil (13.9 g) which is redistilled on a kugelrohr (140–160° C., 0.1 mm Hg) to provide a colorless oil (13.7 g).

Anal. Calcd. for $C_{24}H_{40}OS$: C, 76.53; H, 10.71 Found: C, 76.42; H, 10.77.

EXAMPLE 5

Phenol, 2,6-bis(1,1-dimethylethyl)-4-[(3,7-dimethyloctyl)oxy]-, (MDL 104,102)

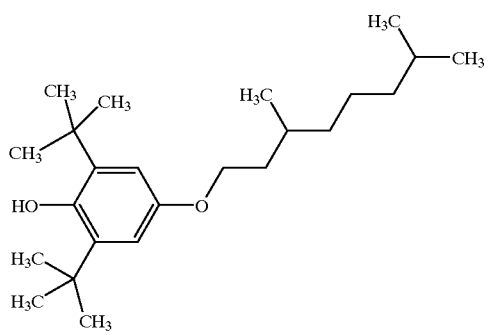

Mix di-t-butyl-1,4-hydroquinone (10.0 g, 45 mmol), bromo-3,7-dimethyloctane (10.0 g, 45 mmol), potassium carbonate (6.22 g, 45 mmol) and acetonitrile (200 mL, degassed under argon), heat to reflux with stirring under argon atmosphere and allow the solvent to distill off until the temperature of the reaction mixture reaches 82° C. Reflux the reaction mixture under argon for an additional three days. Cool dilute the mixture with water and extract with diethyl ether. Wash the ether layer with water and evaporate to dryness to give an oil (16.6 g). Distill the oil in a kugelrohr. Starting material (5.0 g, ~65–110° C., 0.1 mm Hg) may be collected prior to collection of other fractions. An additional fraction collected (135–155° C., 0.1 mm Hg) gives an oil (12.0 g) which is followed by chromatography on silica gel (chloroform). The oil is redistilled on a kugelrohr (138–170° C., 0.1 mm Hg) followed by chromatography on silica gel ($CHCl_3$) to provide an oil (11.7 g). Redistill the resulting product on a kugelrohr (130–145° C., 0.1 mm Hg) to provide an oil (10.7 g) and redistill a final time (130–145° C., 0.1 mm Hg) to give the title compound (10.1 g).

Anal. Calcd. for $C_{24}H_{42}O_2$: C, 79.50; H, 11.68 Found: C, 80.24; H, 11.88.

EXAMPLE 6

Phenol, 2-(1,1-dimethylethyl)-4-[(3,7-dimethyloctyl)oxy]-, (MDL 104,191)

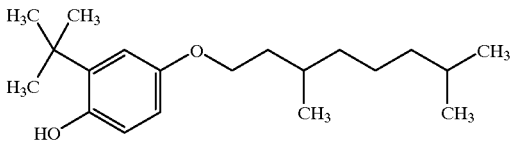

Stir a mixture of 2-t-butyl-hydroquinone (8.3 g, 0.05 mol) and dimethylacetamide (100 mL) under positive argon in an ice bath. Add sodium hydride (2.0 g, 60% dispersion in oil, 0.05 mol) and stir the reaction mixture for 1 hr (and/or evolution of $H_2$ stopped). Add 1-bromo-3,7-dimethyloctane (11.1 g, 0.05 mol) and allow the mixture to warm to room temperature. Allow the precipitate which forms to dissolve (~3 hrs.). Stir the dark brown mixture at room temperature overnight, dilute with $H_2O$ and diethyl ether. Extract the ether layer, wash and evaporate to dryness to provide a brown semi-solid product (16.4 g). Distill the brown semi-solid product in a kugelrohr. Starting material (3.4 g, to 120° C., 0.1 mm Hg) may be collected prior to collection of other fractions. A product fraction collected (~130–155° C., 0.1 mm Hg) gives an oil (~6.5 g). Collect another product fraction (150–185° C., 0.1 mm Hg) to give an oil (~4.1 g). Combine the two product fractions (~6.5 g+~4.1 g) with an additional product fraction from a previous run of the same example (~4.6 g) and evaporate to dryness to give an oil (~15.5 g). Purify the oil by silica gel chromatography eluting sequentially with hexane (500 mL), $CCl_4$:hexane (500 mL, 1:1) and $CCl_4$ to a straw colored oil (9.2 g). Distill the straw colored oil in a kugelrohr and collect the title compound (7.9 g, 135–150° C., 0.1 mm Hg).

EXAMPLE 7

Phenol, 2,6-bis(1,1-dimethylethyl)-4-[(7-hydroxy-3,7-dimethyloctyl)thio]-, (MDL 104,487)

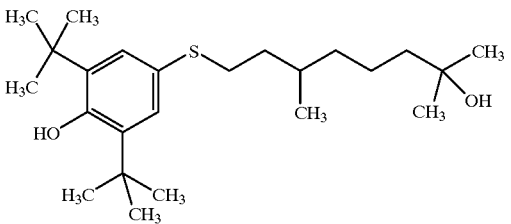

Step a: Preparation of Structure (3a)

Mix hydroxycitronellol (10.0 g, 57.4 mmol), lithium bromide (10.0 g, 111.5 mmol), 2,4,6-collidine (7.0 g, 7.6 mL, 57.7 mmol) and dimethylformamide (100 mL) and stir at room temperature. Add methanesulfonyl chloride (6.6 g, 4.44 mL, 57.4 mmol) over approximately five minutes and stir the mixture overnight at room temperature. Add additional lithium bromide (5.0 g), methanesulfonyl chloride (4.4 mL) and 2,4,6-collidine (7.6 mL) and stir the mixture for four days. Dilute the mixture with $H_2O$ and ether, extract the ether layer wash with saturated $Cu(NO_3)_2$ and water and evaporate to dryness to provide the title compound as a light yellow oil (8.7 g, 37 mmol).

Step b: Preparation of MDL 104,487

Combine the product of Example 7, step a with a mixture of 2,6-di-t-butyl-4-mercaptophenol (8.8 g, 37 mmol), potassium bicarbonate (3.7 g, 37 mmol) and isopropanol (100 mL) and heat to reflux. Continue to reflux the mixture for one hour and allow the solvent to distill off until the temperature of the reaction mixture reaches 82° C. Dilute the reaction mixture with $H_2O$, acidify with conc. hydrochloric acid and extract with diethyl ether. Wash the ether layer with water and brine, filter through silica gel/$Na_2SO_4$ and evaporate to dryness to provide an oil (37.0 g). Distill the oil in a kugelrohr. Starting material (~100–130° C., 0.1 mm Hg) may be collected prior to collection of other fractions. An additional fraction collected (160–175° C., 0.1 mm Hg) provides a residue (13.8 g). Purify the residue by silica gel chromatography eluting sequentially with $CCl_4$, $CCl_4$:$CH_2Cl_2$ (1:1), and $CH_2Cl_2$ to obtain the title compound as a yellow oil (10.6 g).

Anal. Calcd. for $C_{24}H_{42}O_2S$: C, 73.04; H, 10.73 Found: C, 73.19; H, 10.92.

EXAMPLE 8

Phenol, 2,6-bis(1,1-dimethylethyl)-4-[(3,7-dimethyl-6-octenyl)oxy]-, (R)- (MDL 104,535)

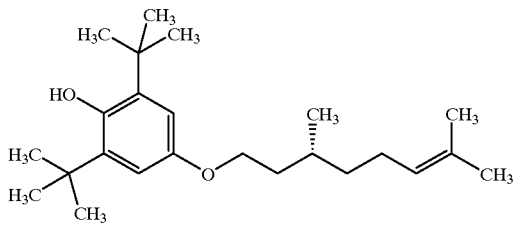

Stir a mixture of 2,6-di-t-butyl-1,4-hydroquinone (6.7 g, 30 mmol), R-(−)-citronellyl bromide (6.6 g, 6.0 mL, 30 mmol) and acetonitrile (150 mL, degassed under argon) at room temperature and add potassium carbonate (4.2 g, 30 mmol). Heat the mixture to reflux under positive argon and reflux overnight. Reflux the reaction mixture an additional 24 hours, add potassium iodide and reflux for an additional ~6 hrs. Cool the reaction mixture to room temperature, dilute with water, acidify with conc. hydrochloric acid, extract with diethyl ether, filter through silica gel/$Na_2SO_4$ and evaporate to dryness to provide an oil (11.0 g). Distill the oil in a kugelrohr. Collect fractions (10.8 g, 120–130° C., 0.1 mm Hg and 150–180° C., 0.1 Hg) and redistill oil in the kugelrohr. An additional fraction collected (160–175° C., 0.1 mm Hg) provides a residue (13.8 g). Collect starting material (2.2 g, up to 120° C., 0.1 mm Hg) and title compound as a light yellow oil (8.3 g, 135–150° C., 0.1 mm Hg).

Anal. Calcd. for $C_{24}H_{40}O_2$: C, 79.94; H, 11.18 Found: C, 79.96; H, 11.10.

EXAMPLE 9

Phenol, 2-(1,1-dimethylethyl)-4-[(3,7-dimethyl-6-octenyl)oxy]-, (MDL 105,411)

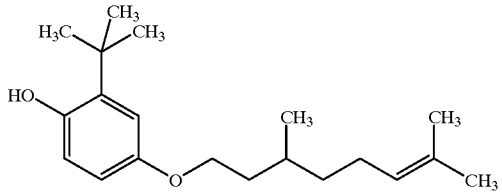

Stir a mixture of 2-t-butylhydroquinone (7.0 g, 42 mmol), R-(−)-citronellyl bromide (9.2 g, 42 mmol) and acetonitrile (150 mL, degassed under vacuum) at room temperature. Add potassium carbonate (5.8 g, 42 mmol) and reflux the mixture with stirring under positive argon overnight. Add potassium iodide (2.0 g) and continue refluxing for three days. Cool the reaction mixture to room temperature, dilute with water, acidify with conc. hydrochloric acid, extract with diethyl ether, filter through silica gel/$Na_2SO_4$ and evaporate to dryness to provide an oil (13.0 g). Distill the oil in a kugelrohr. Collect starting material (1.3 g, up to 120° C., 0.1 mm Hg). An additional fraction collected (140–170° C., 0.1 mm Hg) provides a residue (8.9 g) which is redistilled, collected (7.5 g, 140–160°, 0.1 mm Hg) and purified using silica gel chromatography eluting with $CHCl_3$ to provide the title compound as a light yellow oil (7.1 g).

Anal. Calcd. for $C_{20}H_{32}O_2$: C, 78.89; H, 10.60 Found: C, 79.73; H, 10.86.

EXAMPLE 10

Phenol, 2,5-bis(1,1-dimethylethyl)-4-[(3,7-dimethyl-6-octenyl)oxy]-, (S)- (MDL 107,059)

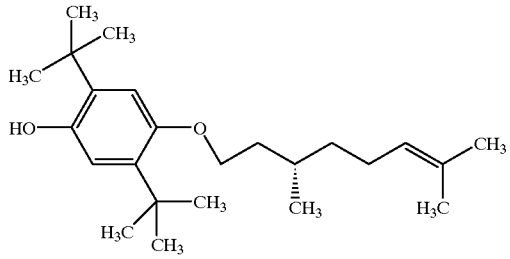

Heat to reflux a mixture of 2,5-di-t-butyl-1,4-hydroquinone (11.1 g, 50 mmol), S-(+)-citronellyl bromide (11.0 g, 50 mmol), potassium carbonate (6.9 g) and acetonitrile (150 mL, degassed under argon) with stirring for two days. Add dimethylformamide (~15 mL) and sodium iodide (~0.5 g) and continue the refluxing overnight. Cool the reaction mixture to room temperature, dilute with water, acidify with conc. hydrochloric acid, extract with diethyl ether, filter through silica gel/$Na_2SO_4$ and evaporate to dryness to provide an oil (19.2 g). Mix the oil with hexane. Filter resulting precipitate. Evaporate to dryness the filtrate and distill the residue in a kugelrohr. Collect starting material (up to 120° C., 0.1 mm Hg). Collect an additional fraction (155–180° C., 0.1 mm Hg) to provide an oil (9.2 g) which is purified using silica gel chromatography (hexane:$CH_2Cl_2$: 4:1) and evaporated to dryness to provide a light straw oil (8.4 g). Redistill the light straw oil in a kugelrohr to provide the title compound as an oil (8.2 g, 150–165° C., 0.1 mm Hg).

Anal. Calcd. for $C_{24}H_{40}O_2$: C, 79.94; H, 11.18 Found: C, 80.68; H, 11.08.

EXAMPLE 11

Butanoic acid, 2,6-bis(1,1-dimethylethyl)-4-[(3,7-dimethyloctyl)oxy]phenyl ester

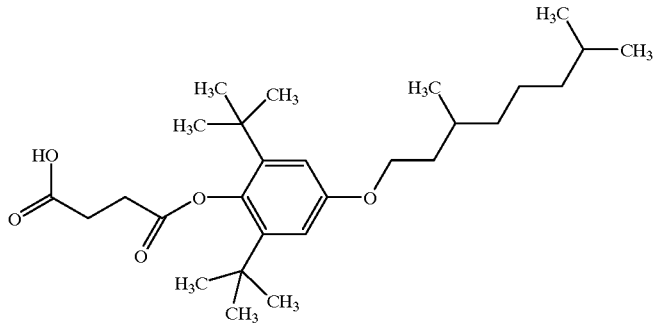

Stir a mixture of the product of Example 5 (4.9 g, 13.5 mmol) and sodium hydride (0.6 g of 60% in oil, 15 mmol) in dimethylacetamide (100 mL) at room temperature for 1 hour. Add monoethylsuccinylchloride (2.46 g, 15 mmol) to the reaction mixture with stirring. Stir the reaction mixture at room temperature overnight then heat at 90° C. for 2 hours and allow to cool. Dilute the mixture with water and extract with ether. Wash the ether layer with water and evaporate to dryness to give a residue. Combine the residue with methanol (100 mL) and heat to reflux. Add sodium hydroxide (1.0 g in 20 mL water) and reflux the reaction mixture for 30 minutes then dilute with water and allow to cool. Acidify the aqueous suspension with conc. hydrochloric acid and extract the mixture with ether and tetrahydrofuran. Separate the organic layer and evaporate to dryness to give the title compound which is crystallized from hexane.

EXAMPLE 12

Acetic acid, 2,6-bis(1,1-dimethylethyl)-4-[(3,7-dimethyl-6-octenyl)oxy]phenyl ester, (S)-

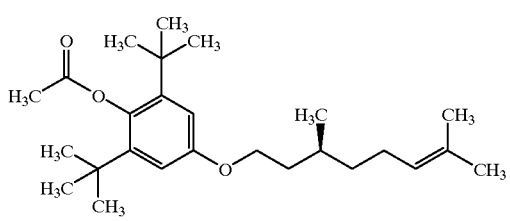

Stir a mixture of the product of Example 1 (6.02 g, 16.7 mmol), sodium hydride (0.67 g of 60% in oil, 16.7 mmol) and dimethylacetamide (50 mL) at room temperature for 30 minutes. Slowly add acetyl chloride (2.6 g, 33.5 mmol) to the reaction mixture and continue the reaction overnight. Dilute the reaction mixture with water and ether and separate the layers. Evaporate the ether layer to dryness to give crude title compound. Distill in a kugelrohr followed by recrystallization to give the title compound.

EXAMPLE 13

Acetic acid, 2-(1,1-dimethylethyl)-4-[(3,7-dimethyl-6-octenyl)oxy]phenyl ester

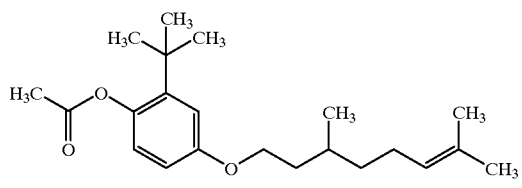

Stir a mixture of the product of Example 9 (4.67 g, 15.3 mmol), triethylamine (3.04 g, 30 mmol) and ether (100 mL) at room temperature. Slowly add acetyl chloride (2.4 g, 30 mmol) with stirring. Stir the mixture for 4 hours then dilute with water. Separate the layers and evaporate the organic layer to dryness to give a residue. Distill the residue in a kugelrohr to provide the title compound.

EXAMPLE 14

Propionic acid, 2,5-bis(1,1-dimethylethyl)-4-[(3,7-dimethyl-6-octenyl)oxy]phenyl ester, (S)-

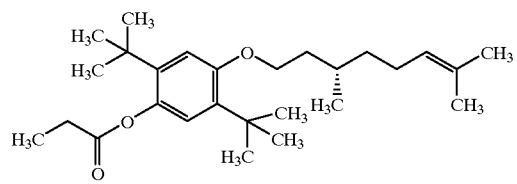

Stir a mixture of the product of Example 10 (7.21 g, 20 mmol), triethylamine (2.53 g, 25 mmol) in ether (150 mL) at room temperature. Add propionyl chloride (23 g, 25 mmol) and stir the mixture overnight. Add water and ether and separate the layers. Evaporation of the organic layer gives an oil which is then distilled in a kugelrohr. The residue may be purified using silica gel chromatography to provide the title compound.

EXAMPLE 15

Butyric acid, 2,6-bis(1,1-dimethylethyl)-4-[(3,7-dimethyl-6-octenyl)thio]phenyl ester

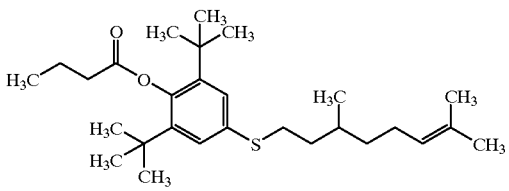

Stir a mixture of the product of Example 4 (7.53 g, 20 mmol), triethylamine (2.53 g, 25 mmol) in ether (150 mL) at room temperature. Add butyryl chloride (2.66 g, 25 mmol) and stir the mixture overnight. Add water and ether and separate the layers. Evaporation of the organic layer gives an oil which is then distilled in a kugelrohr. The residue may be purified using silica gel chromatography to provide the title compound.

EXAMPLE 16

Phenol, 2,3,6-trimethyl-4-[(3,7-dimethyl-6-octenyl)oxy]-, (S)-

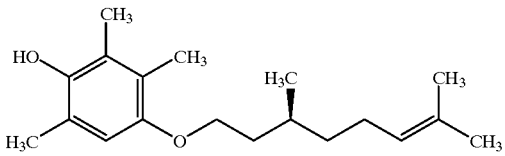

Heat to reflux a mixture of trimethylhydroquinone (10.0 g, 66 mmol, Aldrich Chemical Co., Milwaukee, Wis. 53233), S-(+)-citronellyl bromide (14.47 g, 66 mmol), potassium carbonate (9.12 g, 66 mmol), sodium iodide (9.9 g), and acetonitrile (150 mL) and stir for five days. Cool the mixture, dilute with water and ether and separate the layers. Evaporate the organic layer to dryness to give an oil. Distill the oil in a kugelrohr. Purify the residue using silica gel chromatography and redistill to provide the title compound.

EXAMPLE 17

Phenol, 2,3,5-trimethyl-4-[(3,7-dimethyl-6-octenyl)oxy]-, (S)-

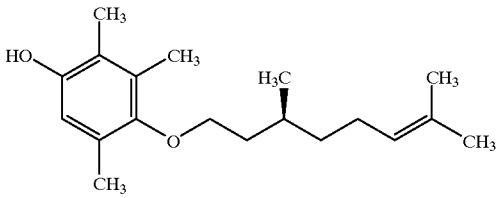

Chromatography of the above reaction product of example 16 followed by distillation yields the title compound.

EXAMPLE 18

Phenol, 2,6-bis(1,1-dimethylethyl)-4-[(3-methyl-2-butenyl)thio]-,

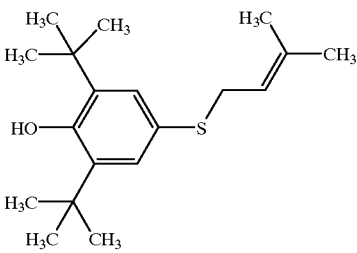

Prepare by the method of Example 4 using 4-bromo-2-methyl-2-butene (6.25 g, 41.9 mmol). Distill in a kugelrohr to give the title compound.

EXAMPLE 19

Phenol, 2-(1,1-dimethylethyl)-4-[(3-methylbutane)oxy]-,

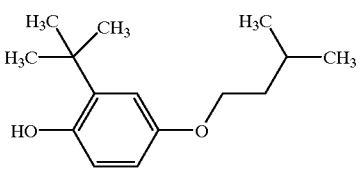

Prepare by the method of Example 6 using 1-bromo-3-methylbutane (7.55 g, 0.05 mol). Distill in a kugelrohr to give the title compound.

EXAMPLE 20

Acetic acid, 2,3,6-trimethyl-4-[(3,7-dimethyl-6-octenyl)oxy]phenyl ester, (S)-

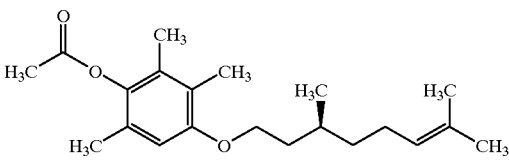

Step a: Preparation of 4-acetoxy-2,3,5-trimethylphenol
Stir a mixture of trimethylhydroquinone (15.2 g, 0.1 mol), triethylamine (25.3 g, 0.25 mol) and ether (500 mL) in an ice bath. Slowly add acetylchloride (19.6 g, 0.25 mol) with stirring, allow the reaction to warm to room temperature for an hour, then dilute with water and the separate the layers. Evaporate the ether layer to dryness. Dissolve the resulting diacetate in methanol (300 mL). Add strong ammonium hydroxide (11 mL) and stir the mixture at room temperature overnight. Distill off the solvents under reduced pressure and dissolve the residue in ether. Wash the ether layer with water and evaporate to dryness. Recrystallization from hexane-ether yields 4-acetoxy-2,3,5-trimethylphenol (16.7 g, m.p.= 106–107° C.).

Step b: Preparation of Acetic acid, 2,3,6-trimethyl-4-[(3,7-dimethyl-6-octenyl)oxy]phenyl ester, (S)-
Heat to reflux a mixture of 4-Acetoxy-2,3,5-trimethylphenol (8.1 g, 41.7 mmol), S-(+)-citronellyl bromide (9.14 g, 41.7 mmol), lithium bromide (3.6 g, 41.7 mmol), potassium carbonate (5.8 g, 41.7 mmol) and acetonitrile (150 mL) with stirring for three days. Cool the mixture, dilute with water, acidify with conc. hydrochloric acid and extract into ether. Evaporate the ether layer to dryness to give a residue. Distill the residue in a followed by chromatography on silica gel to yield the title compound.

The following compounds can be prepared by procedures analogous to those described above in Examples 1–20:
Phenol, 2,6-diethyl-4-[(3,7-dimethyl-6-octenyl)oxy]-,
Phenol, 2,6-diethyl-4-[(3,7-dimethyl-6-octenyl)oxy]-, (S)-
Phenol, 2,6-diethyl-4-[(3,7-dimethyl-6-octenyl)oxy]-, (R)-
Phenol, 2,6-diethyl-4-[(3,7-dimethyl-6-octenyl)thio]-,
Phenol, 2,6-diethyl-4-[(3,7-dimethyl-6-octenyl)thio]-, (S)-
Phenol, 2,6-diethyl-4-[(3,7-dimethyl-6-octenyl)thio]-, (R)-
Phenol, 2,6-diethyl-4-[(3,7-dimethyloctyl)oxy]-,
Phenol, 2,6-diethyl-4-[(7-hydroxy-3,7-dimethyloctyl)oxy]-,
Phenol, 2,5-diethyl-4-[(3,7-dimethyl-6-octenyl)oxy]-,
Phenol, 2,5-diethyl-4-[(3,7-dimethyl-6-octenyl)oxy]-, (S)-
Phenol, 2,5-diethyl-4-[(3,7-dimethyl-6-octenyl)oxy]-, (R)-
Phenol, 2,5-diethyl-4-[(3,7-dimethyl-6-octenyl)thio]-,
Phenol, 2,5-diethyl-4-[(3,7-dimethyl-6-octenyl)thio]-, (S)-
Phenol, 2,5-diethyl-4-[(3,7-dimethyl-6-octenyl)thio]-, (R)-
Phenol, 2,5-diethyl-4-[(3,7-dimethyloctyl)oxy]-,
Phenol, 2,5-diethyl-4-[(7-hydroxy-3,7-dimethyloctyl)oxy]-,
Phenol, 2,6-dipropyl-4-[(3,7-dimethyl-6-octenyl)oxy]-,
Phenol, 2,6-dipropyl-4-[(3,7-dimethyl-6-octenyl)oxy]-, (S)-
Phenol, 2,5-dipropyl-4-[(3,7-dimethyl-6-octenyl)oxy]-, (R)-
Phenol, 2,5-dipropyl-4-[(3,7-dimethyl-6-octenyl)thio]-,
Phenol, 2,6-diisopropyl-4-[(3,7-dimethyl-6-octenyl)thio]-, (S)-
Phenol, 2,6-diisopropyl-4-[(3,7-dimethyl-6-octenyl)thio]-, (R)-
Phenol, 2,5-diisopropyl-4-[(3,7-dimethyloctyl)oxy]-,
Phenol, 2,5-diisopropyl-4-[(7-hydroxy-3,7-dimethyloctyl)oxy]-,
Phenol, 2,3,6-trimethyl-4-[(3,7-dimethyl-6-octenyl)oxy]-,
Phenol, 2,3,6-trimethyl-4-[(3,7-dimethyl-6-octenyl)oxy]-, (R)-
Phenol, 2,3,6-trimethyl-4-[(3,7-dimethyl-6-octenyl)thio]-
Phenol, 2,3,6-trimethyl-4-[(3,7-dimethyl-6-octenyl)thio]-, (S)-
Phenol, 2,3,6-trimethyl-4-[(3,7-dimethyl-6-octenyl)thio]-, (R)-
Phenol, 2,3,6-trimethyl-4-[(3,7-dimethyloctyl)oxy]-,
Phenol, 2,3,6-trimethyl-4-[(7-hydroxy-3,7-dimethyloctyl)oxy]-,
Phenol, 2,3,5-trimethyl-4-[(3,7-dimethyl-6-octenyl)oxy]-,
Phenol, 2,3,5-trimethyl-4-[(3,7-dimethyl-6-octenyl)oxy]-, (R)-
Phenol, 2,3,5-trimethyl-4-[(3,7-dimethyl-6-octenyl)thio]-
Phenol, 2,3,5-trimethyl-4-[(3,7-dimethyl-6-octenyl)thio]-, (S)-
Phenol, 2,3,5-trimethyl-4-[(3,7-dimethyl-6-octenyl)thio]-, (R)-
Phenol, 2,3,5-trimethyl-4-[(3,7-dimethyloctyl)oxy]-,
Phenol, 2,3,5-trimethyl-4-[(7-hydroxy-3,7-dimethyloctyl)oxy]-,
Phenol, 2,5-bis(1,1-dimethylethyl)-4-[(3-methyl-2-butenyl)thio]-,
Phenol, 2-(1,1-dimethylethyl)-4-[(3-methyl-2-butenyl)thiol]-,
Phenol, 2,3,6-trimethyl-4-[(3-methyl-2-butenyl)thiol]-,
Phenol, 2,6-bis(1,1-dimethylethyl)-4-[(3-methylbutyl)oxy]-,
Phenol, 2,5-bis( 1,1-dimethylethyl)-4-[(3-methylbutyl)oxy]-,
Phenol, 2,6-bis(1,1-dimethylethyl)-4-[(3-hydroxy-3-methylbutyl)oxy]-,
Acetic acid, 2,6-bis(1,1-dimethylethyl)-4-[(3,7-dimethyl-6-octenyl)oxy]phenyl ester,
Acetic acid, 2,6-bis(1,1-dimethylethyl)-4-[(3,7-dimethyl-6-octenyl)oxy]phenyl ester, (R)-
Acetic acid, 2,6-bis(1,1-dimethylethyl)-4-[(3,7-dimethyl-6-octenyl)thio]phenyl ester,
Acetic acid, 2,6-bis(1,1-dimethylethyl)-4-[(3,7-dimethyl-6-octenyl)thio]phenyl ester, (S)-
Acetic acid, 2-(1,1-dimethylethyl)-4-[(3,7-dimethyl-6-octenyl)thio]phenyl ester, (R)-
Acetic acid, 2,5-bis(1,1-dimethylethyl)-4-[(3,7-dimethyloctyl)oxy]phenyl ester,
Acetic acid, 2,3,6-trimethyl-4-[(7-hydroxy-3,7-dimethyloctyl)oxy]phenyl ester,
Propionic acid, 2,6-bis(1,1-dimethylethyl)-4-[(3,7-dimethyl-6-octenyl)oxy]phenyl ester,
Propionic acid, 2,6-bis(1,1-dimethylethyl)-4-[(3,7-dimethyl-6-octenyl)oxy]phenyl ester, (R)-
Propionic acid, 2,6-bis(1,1-dimethylethyl)-4-[(3,7-dimethyl-6-octenyl)thio]phenyl ester,
Propionic acid, 2,6-bis(1,1-dimethylethyl)-4-[(3,7-dimethyl-6-octenyl)thio]phenyl ester, (S)-
Propionic acid, 2-(1,1-dimethylethyl)-4-[(3,7-dimethyl-6-octenyl)thio]phenyl ester, (R)-
Propionic acid, 2,5-bis(1,1-dimethylethyl)-4-[(3,7-dimethyloctyl)oxy]phenyl ester,
Butyric acid, 2,3,6-trimethyl-4-[(7-hydroxy-3,7-dimethyloctyl)oxy]phenyl ester,
Butyric acid, 2,6-bis(1,1-dimethylethyl)-4-[(3,7-dimethyl-6-octenyl)oxy]phenyl ester,
Butyric acid, 2,6-bis(1,1-dimethylethyl)-4-[(3,7-dimethyl-6-octenyl)oxy]phenyl ester, (R)-
Butyric acid, 2,5-bis(1,1-dimethylethyl)-4-[(3,7-dimethyl-6-octenyl)thio]phenyl ester,
Butanoic acid, 2,6-bis(1,1-dimethylethyl)-4-[(3,7-dimethyl-6-octenyl)thio]phenyl ester, (S)-
Butanoic acid, 2-(1,1-dimethylethyl)-4-[(3,7-dimethyl-6-octenyl)thio]phenyl ester, (R)-
Butanoic acid, 2,5-bis(1,1-dimethylethyl)-4-[(3,7-dimethyloctyl)oxy]phenyl ester,
Butanoic acid, 2,3,6-trimethyl-4-[(7-hydroxy-3,7-dimethyloctyl)oxy]phenyl ester.

A general synthetic scheme for preparing compounds of formula (1) wherein Z is ethylene is set forth in Scheme B, wherein all substituents, unless otherwise indicated are as previously defined.

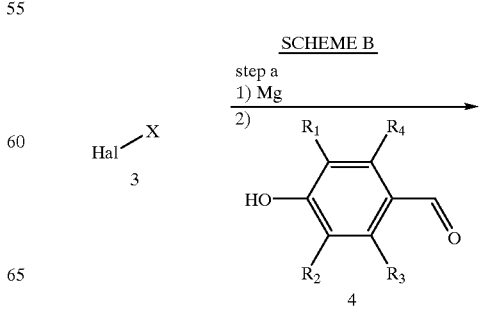

19
-continued

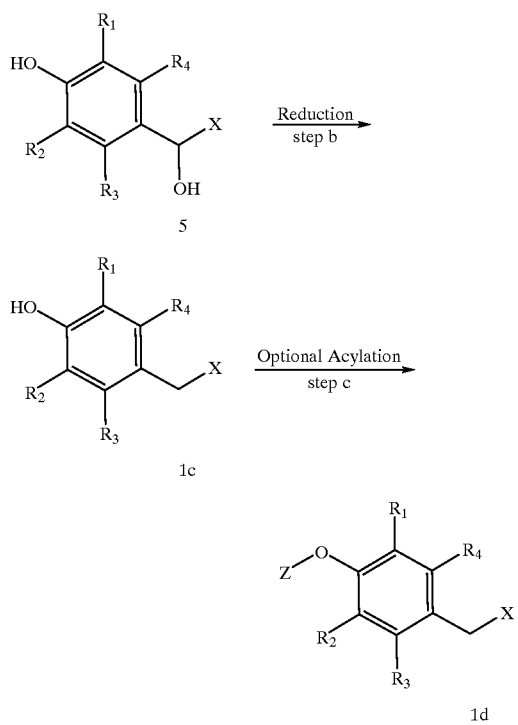

Hal = chlorine, bromine or iodine

In general, a phenol of structure 1c can be prepared according to Scheme B in a two-step process. In step a, the appropriate appropriate haloalkane or haloalkene of structure 3 is reacted with magnesium metal in a suitable aprotic solvent, such as ethyl ether, in order to form the magnesium halide salt. The magnesium halide salt (Grignard reagent) is then reacted with the appropriate alkyl-4-hydroxybenzaldehyde of structure 4 (or a suitably protected derivative) to give the alcohol of structure 5. In step b, the alcohol of structure 5 can be reduced to the desired phenol of structure 1b by a variety of reduction techniques and procedures as are well known and appreciated in the art. For example, the alcohol of structure 5 can be reduced by means of a Birch reduction by reacting it with sodium in liquid ammonia.

A phenol ester of structure 1d can be prepared by acylating a phenol of structure 1c according to standard acylation techniques as described previously in Scheme A.

Starting materials for use in the general synthetic procedures outlined in Scheme B are readily available or can readily be prepared according to standard techniques and procedures. Where necessary to prevent undesired side reactions, the 1-phenol functionality of the alkyl-4-hydroxybenzaldehyde of structure 4 in Scheme B may be blocked prior to the Grignard reaction with a standard phenol blocking agent as described previously in Scheme A.

The following example presents a typical synthesis as described in Scheme B. This example is understood to be illustrative only and is not intended to limit the scope of the present invention in any way.

20
EXAMPLE 21

Phenol, 2,3,6-trimethyl-4-(4,8-dimethyl-7-nonenyl)-, (R)-

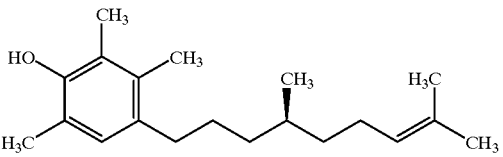

Step a

Mix magnesium turnings (240 mg, 10 mmol) and anhydrous ethyl ether under an inert atmosphere. Add a solution of S-(+)-citronellyl bromide (2.19 g, 10 mmol) in anhydrous ethyl ether. Stir until the magnesium metal dissolves. Add a solution of 2,3,5-trimethyl-4-hydroxybenzaldehyde (1.7 g, 10 mmol) in anhydrous ethyl ether. Stir until reaction is complete. Cool the reaction mixture to 0° C. and add saturated ammonium chloride solution. Separate the ether layer, wash with water and dry ($MgSO_4$). Evaporate to the appropriate intermediate of structure 5 and purify by silica gel chromatrography.

Step b

Mix sodium metal (520 mg, 22.6 mmol) and liquid ammonia (13 mL). To this solution add, by dropwise addition, a solution of the intermediate of Example 19, step a (3.04 g, 10 mmol) in ethyl alcohol (0.5 g) and ethyl ether (5 ml). After the blue color disappears, cautiously add water (13 mL), extract with ethyl ether, dry ($MgSO_4$), and evaporate the solvent. Purify the residue by silica gel chromatography to yield the title compound.

Alternatively, compounds of formula (1) wherein Z is methylene can be prepared according to the procedure set forth in Scheme C, wherein all substituents, unless otherwise indicated, are previously described.

SCHEME C

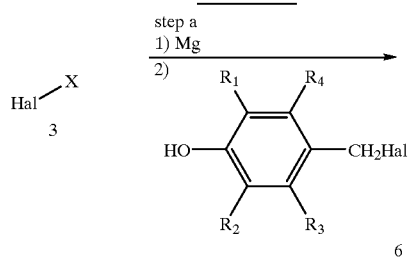

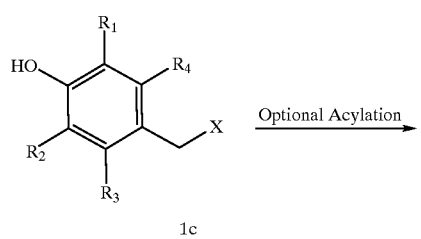

21
-continued

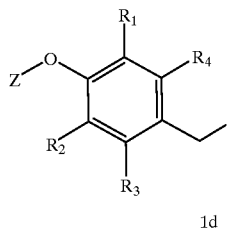

1d

Hal = chlorine, bromine or iodine

In general, a phenol of structure 1b can be prepared by first reacting the appropriate haloalkane or haloalkene of structure 3 with magnesium metal in an suitable aprotic solvent, such as ethyl ether, in order to form the magnesium halide salt. The magnesium halide salt (Grignard Reagent) is then reacted with the appropriate alkyl-4-hydroxy-benzylhalide of structure 6 (or a suitably protected derivative) to give the desired phenol of structure 1c.

A phenol ester of structure 1d can be prepared by acylating a phenol of structure 1c according to standard acylation techniques as described previously in Scheme A.

Starting materials for use in the general synthetic procedures outlined in Scheme C are readily available or can readily be prepared according to standard techniques and procedures. For example, the preparation of 3,5-dimethyl-4-acetoxy-benzylbromide is described in *Tetrahedron* 33, 3097–103 (1977). 3,5-Dimethyl-4-acetoxy-benzylbromide can be converted to the corresponding phenolic starting material by standard hydrolytic procedures.

Where necessary to prevent undesired side reactions, the 1-phenol functionality of the alkyl-4-hydroxy-benzylhalide of structure 6 in Scheme C may be blocked prior to the Grignard reaction with a standard phenol blocking agent as described previously in Scheme A.

The following examples present typical syntheses as described in Scheme C. These examples are understood to be illustrative only and are not intended to limit the scope of the present invention in any way.

EXAMPLE 22

Phenol, 2,6-diethyl-4-(4,8-dimethyl-7-nonenyl)-, (R)-

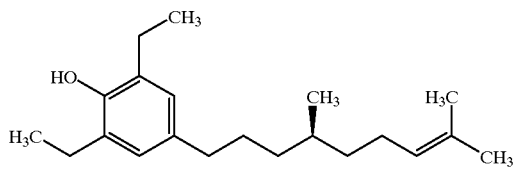

Mix magnesium turnings (240 mg, 10 mmol) and anhydrous ethyl ether under an inert atmosphere. Add a solution of S-(+)-citronellyl bromide (2.19 g, 10 mmol) in anhydrous ethyl ether. Stir until the magnesium metal dissolves. Add a solution of 4-bromomethyl-2,6-diethylphenol (2.43 g, 10 mmol) in anhydrous ethyl ether and reflux the mixture until the reaction is complete. Pour onto a mixture of ice/hydrochloric acid and separate the layers. Wash the ethereal layer with water, dry (MgSO$_4$) and evaporate to give the title compound which is purified by silica gel chromatography.

22

EXAMPLE 23

Acetic Acid, 2,6-diethyl-4-[(4,8-dimethyl-7-nonenyl)-, (R)-

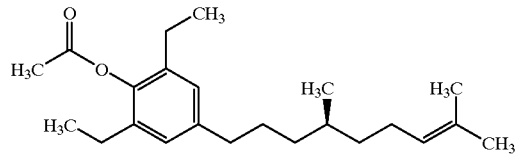

Stir a mixture of the product of Example 20 (6.05 g, 20 mmol), triethylamine (2.53 g, 25 mmol) in ether (150 ml) at room temperature. Add acetyl chloride (1.96 g, 25 mmol) and stir the mixture overnight. Add water and ether and separate the layers. Evaporation of the organic layer gives an oil which is distilled in a kugelrohr. Chromatography on silica gel (chloroform) gives the title compound.

The following compounds can be prepared by procedures analogous to those described above in Examples 21–23:

Phenol, 2,6-bis(1,1-dimethylethyl)-4-(4,8-dimethyl-7-nonenyl)-,
Phenol, 2,6-bis(1,1-dimethylethyl)-4-(4,8-dimethyl-7-nonenyl)-, (R)-,
Phenol, 2,6-bis(1,1-dimethylethyl)-4-(4,8-dimethyl-7-nonenyl)-, (S)-,
Phenol, 2,6-bis(1,1-dimethylethyl)-4-(4,8-dimethylnonyl)-,
Phenol, 2,6-bis(1,1-dimethylethyl)-4-(4,8-dimethylnonyl)-, (R)-,
Phenol, 2,6-bis(1,1-dimethylethyl)-4-(4,8-dimethylnonyl)-, (S)-,
Benzeneoctanol, 3,5-bis(1,1-dimethylethyl)-4-hydroxy-α,α,ε-trimethyl-,
Benzeneoctanol, 3,5-bis(1,1-dimethylethyl)-4-hydroxy-α,α,ε-trimethyl-, (R)-,
Benzeneoctanol, 3,5-bis(1,1-dimethylethyl)-4-hydroxy-α,α,ε-trimethyl-, (S)-,
Phenol, 2,5-bis(1,1-dimethylethyl)-4-(4,8-dimethyl-7-nonenyl)-,
Phenol, 2,5-bis(1,1-dimethylethyl)-4-(4,8-dimethyl-7-nonenyl)-, (R)-,
Phenol, 2,5-bis(1,1-dimethylethyl)-4-(4,8-dimethyl-7-nonenyl)-, (S)-,
Phenol, 2,5-bis(1,1-dimethylethyl)-4-(4,8-dimethylnonyl)-,
Phenol, 2,5-bis(1,1-dimethylethyl)-4-(4,8-dimethylnonyl)-, (R)-,
Phenol, 2,5-bis(1,1-dimethylethyl)-4-(4,8-dimethylnonyl)-, (S)-,
Benzeneoctanol, 3,6-bis(1,1-dimethylethyl)-4-hydroxy-α,α,ε-trimethyl-,
Benzeneoctanol, 3,6-bis(1,1-dimethylethyl)-4-hydroxy-α,α,ε-trimethyl-, (R)-,
Benzeneoctanol, 3,6-bis(1,1-dimethylethyl)-4-hydroxy-α,α,ε-trimethyl-, (S)-,
Phenol, 2-(1,1-dimethylethyl)-4-(4,8-dimethyl-7-nonenyl)-,
Phenol, 2-(1,1-dimethylethyl)-4-(4,8-dimethyl-7-nonenyl)-, (R)-,
Phenol, 2-(1,1-dimethylethyl)-4-(4,8-dimethyl-7-nonenyl)-, (S)-,
Phenol, 2-(1,1-dimethylethyl)-4-(4,8-dimethylnonyl)-,
Phenol, 2-(1,1-dimethylethyl)-4-(4,8-dimethylnonyl)-, (R)-,
Phenol, 2-(1,1-dimethylethyl)-4-(4,8-dimethylnonyl)-, (S)-,
Benzeneoctanol, 3-(1,1-dimethylethyl)-4-hydroxy-α,α,ε-trimethyl-,
Benzeneoctanol, 3-(1,1-dimethylethyl)-4-hydroxy-α,α,ε-trimethyl-, (R)-, Benzeneoctanol, 3-(1,1-dimethylethyl)-4-hydroxy-α,α,ε-trimethyl-, (S)-,
Benzeneoctanol, 4-(acetoxy)-3,5-bis(1,1-dimethylethyl)-α,α,ε-trimethyl-,
Benzeneoctanol, 4-(acetoxy)-3,5-bis(1,1-dimethylethyl)-α,α,ε-trimethyl-, (R)-,
Benzeneoctanol, 4-(acetoxy)-3,5-bis(1,1-dimethylethyl)-α,α,ε-trimethyl-, (S)-,
Benzeneoctanol, 4-(acetoxy)-3,5-bis(1,1-dimethylethyl)-4-(4,8-dimethyl-7-nonenyl)-,
Benzeneoctanol, 4-(acetoxy)-3,5-bis(1,1-dimethylethyl)-4-(4,8-dimethyl-7-nonenyl)-, (R)-,
Benzeneoctanol, 4-(acetoxy)-3,5-bis(1,1-dimethylethyl)-4-(4,8-dimethyl-7-nonenyl)-, (S)-

It is understood that compounds of formula (1) may exist in various stereoisomeric forms. All stereoisomeric forms which are consistent with the above structural formulas, as interpreted according to standard conventions for expressing stereoisomeric structure, are intended to be included within the scope of the present invention.

Preferred compounds of formula (1) are those in which Z is hydrogen, acetyl or succinyl, preferably hydrogen; $R_1$ is methyl or tertiarybutyl; $R_2$ and $R_3$ are each independently hydrogen, methyl or tertiarybutyl; $R_4$ is hydrogen or methyl. More preferred are the compounds:
Phenol, 2,6-bis(1,1-dimethylethyl)-4-[(3,7-dimethyl-6-octenyl)oxy]-, (S)-,
Phenol, 2-(1,1-dimethylethyl)-4-[(3,7-dimethyl-6-octenyl)oxy]-, (S)-,
Phenol, 2-(1,1-dimethylethyl)-4-[(3,7-dimethyl-6-octenyl)thio]-, (S)-,
Phenol, 2,6-bis(1,1-dimethylethyl)-4-[(3,7-dimethyl-6-octenyl)thio]-,
Phenol, 2,6-bis(1,1-dimethylethyl)-4-[(3,7-dimethyloctyl)oxy]-,
Phenol, 2-(1,1-dimethylethyl)-4-[(3,7-dimethyloctyl)thio]-,
Phenol, 2,6-bis(1,1-dimethylethyl)-4-[(7-hydroxy-3,7-dimethyloctyl)thio]-,
Phenol, 2,6-bis(1,1-dimethylethyl)-4-[(3,7-dimethyl-6-octenyl)oxy]-, (R)-,
Phenol, 2-(1,1-dimethylethyl)-4-[(3,7-dimethyl-6-octenyl)oxy]-, and
Phenol, 2,5-bis(1,1-dimethylethyl)-4-[(3,7-dimethyl-6-octenyl)oxy]-, (S)-.

As used herein, the term "patient" refers to a warm-blooded animal or mammal which is in need of treatment for a chronic inflammatory disease, atherosclerosis, hypercholesterolemia or which is in need of inhibiting cytokine-induced expression of vascular cell adhesion molecule-1 and/or intercellular adhesion molecule-1. It is understood that guinea pigs, dogs, cats, rats, mice, hamsters, rabbits and primates, including humans, are examples of patients within the scope of the meaning of the term.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

An effective antiatherosclerotic amount of a compound of formula (1) is an amount which is effective in inhibiting the development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of atherosclerosis. It is further understood and appreciated by those of ordinary skill in the art that successful treatment for atherosclerosis can include prophylaxis in preventing atherosclerotic lesion or plaque formation.

Peroxidation of LDL lipid, such as the unsaturated fatty acid portions of LDL cholesteryl esters and phospholipids, is known to facilitate the deposition of cholesterol in macrophages which subsequently are deposited in the vessel wall and are transformed into foam cells. The identification of those patients who are in need of inhibition of peroxidation of LDL lipid is well within the ability and knowledge of one of ordinary skill in the art. For example, those individuals who are in need of treatment for atherosclerosis as defined hereinabove, are also patients who are in need of inhibition of peroxidation of LDL lipid. An effective antioxidant amount of a compound of formula (1) is an amount which is effective in inhibiting the peroxidation of LDL lipid in a patient's blood.

Hypercholesterolemia is a disease state characterized by levels of serum cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by use of clinical tests, physical examination and medical/family history, those patients who are suffering from hypercholesterolemia and those who are at risk of developing hypercholesterolemia and thus readily determine if an individual is a patient in need of hypercholesterolemia.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: asthma, chronic inflammation, rheumatoid arthritis, autoimmune diabetes, transplant rejection and tumor angiogenesis. A "therapeutically effective amount" of a compound of formula (1) is an amount which is effective, upon single or multiple dose administration to the patient, in providing relief of symptoms associated with chronic inflammatory diseases. An "effective vascular cell adhesion molecule-1 and/or intercellular cell adhesion molecule-1 inhibiting amount" of a compound of formula (1) is an amount which is effective, upon single or multiple dose administration to the patient, in providing relief of symptoms associated with vascular cell adhesion molecule-1 and/or intercellular adhesion molecule-1 mediated conditions.

As used herein, "relief of symptoms" of a chronic inflammatory disease or vascular cell adhesion molecule-1 mediated conditions refers to decrease in severity over that expected in the absence of treatment and does not necessarily indicate a total elimination or cure of the disease. Relief of symptoms is also intended to include prophylaxis.

In determining the therapeutically effective amount or dose, the effective antioxidant amount or dose, the plasma cholesterol lowering amount or dose, the effective antiatherosclerotic amount or dose or the effective VCAM-1 and/or ICAM-1 inhibiting amount of a compound of formula (1), a number of factors are considered by the attending diagnostician, including, but not limited to: the species of the mammal; its size, age, and general health; the specific disease involved; the degree of or involvment or the severity of the disease; the response of the individual patient; the particular compound administered; the mode of administration; the bioavailability characteristics of the preparation administered; the dose regimen selected; the use of concomitant medication; and other relevant cirmumstances.

A therapeutically effective amount, an effective antioxidant amount, a plasma cholesterol lowering amount, an effective antiatherosclerotic amount or an effective VCAM-1 and/or ICAM-1 inhibiting amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

The compounds of this invention are inhibitors of VCAM-1 and/or ICAM-1 expression. It is believed that the compounds of this invention exert their inhibitory effect through inhibition of VCAM-1 and/or ICAM-1 upregulation by cytokines and thereby prevent or provide relief of symptoms for chronic inflammatory diseases including asthma, chronic inflammation, rheumatoid arthritis, autoimmune diabetes, and the like; atherosclerosis and hypercholesterolemia. However, it is understood that the present invention is not limited by any particular theory or proposed mechanism to explain its effectiveness in an end-use application.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (1): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

EXAMPLE 24

Percent Inhibition of VCAM-1 and ICAM-1 Cytokine-Induced Expression by Selected Phenolic Antioxidants in Human Aortic Smooth Muscle Cells or Proliferating Human Umbilical Vein Endothelial Cells Plate proliferating human umbilical vein endothelial cells (HUVEC) or human aortic smooth muscle cells (HASMC) from Clonetics (San Diego, Calif.) onto 96-well plates in 100 $\mu$L medium per well at 20,000 cells per $cm^2$. Maintain the cultures in growth medium (EGM or SMGM2, Clonetics, San Diego, Calif.) for two days prior to addition of cytokines or drugs. Add cytokines plus or minus compounds for 20 to 24 hours prior to analysis for adhesion molecule levels. Add tumor necrosis factor (Genzyme, Cambridge, Mass.) to cultures at 500–1000 units/mL to stimulate ICAM-1 expression. Add interleukin-4 (GIBCO-BRL, Gaithersburg, Md.) to cultures at 100–200 pg/mL to stimulate VCAM-1 expression. (Make additions by transferring 100 μL of cytokines plus compounds serially diluted on a separate 96-well plate into the plates containing cells. Do not exchange the medium on the cultures prior to addition of effectors). Remove the culture medium, and wash the monolayers twice with Hanks buffered saline solution (HBSS) at room temperature. Add the primary antibody (anti-human VCAM-1 from Upstate Biotechnology, Inc., Lake Placid, N.Y. or anti-human ICAM-1 from Immunotech, Inc., Westbrook, Me.) to each well (1 μg/mL in HBSS plus 5% newborn calf serum, GIBCO-BRL, Gaithersburg, Md.) and incubate at 37° C. for 1 hr. Wash the wells twice with HBSS, then add 100 μL of a 1/1000 dilution of goat anti-mouse IgG conjugated to horse radish peroxidase (BioRad, Hercules, Calif.) in HBSS plus 5% newborn calf serum to each well and incubated for 1 hr at 37° C. Wash the wells three times with HBSS, then add 100 μL of TMB substrate (BioRad, Hercules, Calif.) to each well. Stop the reaction after blue color develops by addition of 50 μL of 1N $H_2SO_4$. Measure absorbance at 450 nm with a plate reader.

Table 1 summarizes the ability of selected compounds of this invention to inhibit VCAM-1 and ICAM-1 using human aortic smooth muscle cells (HASMC). In these experiments, the cells were coincubated with interleukin-4 to stimulate VCAM-1 expression and with tumor necrosis factor-alpha to stimulate ICAM-1 expression.

TABLE 1

Inhibition of VCAM-1 and ICAM-1 in Human Aortic Smooth Muscle Cells (HASMC)

| Cmpd. No. (MDL No.) | VCAM-1 (% inh. 50 μM)* | ICAM-1 (% inh. 50 μM)@ |
|---|---|---|
| 103,960 | 33.9 ± 6 | 0 ± 12 |
| 104,191 | 42.9 ± 7 | 22 ± 0 |
| 104,535 | 26.4 ± 14 | (10 ± 5) |

*Average of three runs
@Average of two runs, numbers in parentheses represent negative values Table 2 summarizes the ability of various compounds of this invention to selectively inhibit VCAM-1 or to inhibit both VCAM-1 and ICAM-1 using proliferating human umbilical vein endothelial cells (HUVEC). In these experiments, the cells were coincubated with tumor necrosis factor-alpha along with the indicated compounds about 20 to 24 hr before assaying cell surface adhesion molecule expression.

TABLE 2

Inhibition of VCAM-1 and/or ICAM-1 in Human Umbilical Vein Endothelial Cells (HUVEC)

| Cmpd. No. (MDL No.) | VCAM-1 (% inh. 50 μM)* | ICAM-1 (% inh. 50 μM)@ |
|---|---|---|
| 103,960 | 25.7 | 9.5 |
| 104,191 | 34.3 | 70.5 |
| 104,535 | (2.5) | 11.5 |

*Average of three runs, numbers in parentheses represent negative values
@Average of two runs In vivo activity of these compounds can also be assessed in other models of inflammation predicted to involve elevated VCAM-1 levels. One such model for respiratory diseases, such as asthma, is an ovalbumin-sensitized model. Kung, T. T. et al., *Int. Arch. Allergy Immunol.* 105, 83–90 (1994). This model of pulmonary inflammation is IgE mediated and involves eosinophillia (as does the asthmatic human). The bronchial alveolar lavage (BAL) fluid obtained from experimental animals can be assessed for a number of parameters, including soluble adhesion molecule expression and leukocyte accumulation. Adhesion molecule expresssion can be assessed by immunohistochemistry within the tissues, especially the lung, of experimental animals. The effect of the claimed compounds should be to suppress the upregulation of VCAM-1 expression and inhibit eosinophil accumulation in the BAL fluid. The inhibitors could be tested in a rat model of adjuvant arthritis, which has been previously shown to respond to anti-ICAM-1 monoclonal antibodies. Iigo, Y. et al., *J. Immunol.* 147, 4167–4171 (1991). In this model, adhesion molecule expression would be assessed in the limbs (joints) of experimental animals. For autoimmune diabetes, one could test the compounds for their ability to delay the onset or prevent adoptive transfer of disease in the NOD mouse model. Heinke, E. W. et al., *Diabetes* 42, 1721–1730 (1993); Baron, J. L. et al., *J. Clin. Invest.* 93, 1700–1708 (1994). Furthermore, one can monitor the level of VCAM-1 expression in the tissues (e.g. pancreas) as well as monitor the development of diabetes in the experimental animal. Therapeutic potential for transplant rejection can be assessed by monitoring cardiac allograft survival (Balb/c hearts transplanted into C3H/He recipients. Isobe, M. et al., *J. Immunol.* 153, 5810–5818 (1994). In vivo administration of anti-VCAM-1 and anti-VLA-4 monoclonal antibodies induces immunosuppression to cardiac allografts and soluble antigens in this mouse model. Compound effects on tumor metastasis and angiogenesis can be evaluated in a number of models. These can include the B16 (murine) and M24met (human) melanoma models for experimental metastasis. Fidler, I. J., *Cancer Res.* 35, 218–224 (1975); Meuller, B. M. et al., *Cancer Res.* 51, 2193–2198. Activity of the compounds can be assessed by their effect on the number of lung metastases which develop, as well as their effect on VCAM-1 expression in the lung as described above for the mouse respiratory model. A model for evaluating anti-angiogenic compounds which can be used to test the compounds involves monitoring the vascular response to a mixture of angiogenic factors mixed with basement membrane proteins injected subcutaneously in mice. Passaniti, A. et al., *Lab. Invest.* 67, 519–528 (1992). Angiogenesis is scored by the number of vessels recruited into the matrigel and by the hemoglobin content of the gels. Adhesion molecule expression and accumulation of leukocyte can be determined by immunohistochemical methods as in all of the above examples.

EXAMPLE 25

Hypochloesterolemic and Antioxidant Effects of Compounds of Formula (1) in Choleterol-Fed Female New Zealand White Rabbits A. Experimental Protocol Perform five independent experiments in the following manner. Each study has a control group and 1–5 groups treated with MDL compound (N=5 per group). Feed Female New Zealand White rabbits (Hazelton, ~2.0–2.3 kg) 0.2% cholesterol enriched rabbit chow (Purina #5322) with or without 0.4% MDL compound. Solubilize the MDL compounds in 100% ethanol. Spray the chow with the MDL mixtures and allow to dry overnight in a chemical fume hood. Spray control chow with ethanol. Feed rabbits 100 grams food per day for 7 days (0.6% MDL 103,491 were fed for 14 days); make available water ad libitum. On day 7, bleed (~2 mL) rabbits (fasted overnight) from a marginal ear vein. Euthanize rabbits by carbon dioxide overdose. Record the total body and liver weights in grams. Record food as grams·days$^{-1}$·rabbits$^{-1}$. Use aliquots of fresh serum for clinical chemistries, lipoprotein cholesterol determination, thiobarbituric acid reactive substances (TBARS) and compound and metabolite concentrations in serum. Freeze livers (~5 gram aliquots) at −20° C. for compound and metabolite concentration determination at a later time.

B. Clinical Chemistries

Allow blood to clot at room temperature for 30 minutes. Obtain serum after centrifugation for 10 min at 5° C. at 3000 rpm in a Beckman GPKR centrifuge with a GH rotor. Analyze by a COBAS MIRA autoanalyzer (Roche Diagnostics) using Roche diagnostic reagents for total cholesterol (CHOL, kit # 44334) and triglyceride (TG, kit # 44120). Calculate cholesterol and triglycerides as mg/dL.

C. TBARS Assay

TBARS are a qualitative indication of the oxidation of lipids in a sample. In this assay initiate the oxidation of serum lipids with $CuSO_4$, resulting in the formation of aldehydes, such as malondialdehyde (MDA). Upon incubation with thiobarbituric acid, the absorbance of the aldehydes can be detected at 530–540 nm. TBARS values which are lower than control serum values indicate the relative ability of a compound to inhibit the oxidation. Measure as follows: mix 50 μL of serum with 50 μL of 0.9% saline and 400 μL of a 5 mM $CuSO_4$ solution and incubate at 37° C. for 5 hr. Stop the reactions by addition of 1.0 mL of 20% trichloroacetic acid. Then add 1.0 mL of 0.67% thiobarbituric acid in 0.05 N sodium hydroxide, mix, and incubate the samples for 30 min at 90° C. Centrifuge the samples briefly to pellet undissolved material, and transfer the supernatants to a 96-well microtiter plate. Measure absorbances at 540 nm using a Biotek model EL311 microplate reader. The nmoles of MDA produced are calculated from a standard curve of 0 to 10 nmoles of MDA prepared from malonaldehyde bis(dimethylacetal). Compare serum samples from treated rabbits to serum samples from control rabbits that received no MDL compound.

D. HPLC Quantitation of Compound and Metabolite Concentration in Serum and Liver Determine serum and liver concentrations of parent compounds and the metabolites, bisphenol and diphenoquinone, by reverse phase HPLC using a Waters 990 Powerline system. Homegenize livers (1 gram) with 5.0 mL PBS, pH 7.4, using a Polytron tissue homogenizer at setting 5 for 20–30 seconds. Extract serum or liver homogenates as follows: add 100 μL of either serum or homogenate to 2.0 mL diethyl ether:ethanol (3:1) while vortexing the tube. Cap the sample tubes and centrifuge for 10 min at 5° C. at 3500 rpm in a Beckman GPKR centrifuge with a GH 3.7 rotor. Transfer the supernatants to clean tubes and dry under $N_2$. Reconstitute samples with 200 μL of acetonitrile:hexane:0.1 M ammonium acetate (90:6.5:3.5, by vol.). Inject 100 μL onto a Waters Deltapak C18-300 Å column, and elute with an 83% acetonitrile:17% water mobile phase at a flow rate of 1.5 mL/min. Record absorbances at the wavelengths of 240, 254, and 420 nm. Calculate compound concentrations from known quantities of authentic parent compounds after correction for recovery. Calculate concentrations as μg/mL of serum and μg/g of liver.

E. HPLC Separation and Quantitation of Lipoprotein Subfraction Cholesterol Levels Separate lipoprotein fractions (very low density lipoprotein, VLDL, low density lipoprotein, LDL and high density lipoprotein, HDL) on a Sepharose 6HR column (1×30 cm, Pharmacia) attached to a Waters Powerline HPLC system. Inject serum (50 μL) onto the column and elute with phosphate buffered saline, pH 7.4, at a flow rate of 0.5 mL/min. Add cholesterol reagent (Roche Diagnostics, kit # 44334, diluted with 20 mL water and then with 20 mL of 0.9% saline) at 0.2 mL/min to the post column eluant and incubate in a knitted PFTE Kratos reaction coil (Applied Biosystems) at 37° C. for 5 min. Measure absorbance at 500 nm. The lipoprotein subfractions are quantitated as follows:

(total serum cholesterol)×(% area under the curve for each subfraction)

Tables 3 and 4 below present summary data from the individual experiments of this testing procedure.

TABLE 3

Hypochloesterolemic and Antioxidant Effects of Compounds of Formula (1) in Cholesterol-Fed Female New Zealand White Rabbits as a Percent of Control

| MDL # | Diet % | food | body wt. | lw/bw | chol tot. | LDL | HDL | TRIG | TBARS |
|---|---|---|---|---|---|---|---|---|---|
| 103,294 | 0.4 | 103% | 100% | 105% | 94% | 82% | 192% | 197% | 35% |

N = 5 rabbits/group; fasted overnight
Rabbits were fed x 7 days
Diet % = (weight MDL compound/weight food) × (100)
The data in Table 3 were normalized as follows:
% Control = (Mean, treated group/Mean, control group) × (100)
Food = grams eaten per day per rabbit
Body wt. = weight in grams
LW/BW = (liver weight/body weight in grams)
CHOL = total cholesterol mg/dL
LDL = Low Density lipoprotein cholesterol mg/dL
HDL = High Density lipoprotein cholesterol mg/dL
TRIG = triglycerides, mg/dL
TBARS = thiobarbituric acid reactive substances, expressed as nmole MDA

TABLE 4

Drug and Metabolite Concentration in Rabbit Serum and Liver

| | | Serum | | | Liver | | |
|---|---|---|---|---|---|---|---|
| MDL # | Diet % | Parent | Bis | Quin | Parent | Bis | Quin |
| 103,294 | 0.4 | 19.8 | 0 | 0 | 77 | 0 | 0 |

N = 5 rabbits/group; fasted overnight
Rabbits were fed × 7 days
Diet % = (weight MDL compound/weight food) × (100)
The data in Table 4 are presented as Means (N = 5) and have not been normalized to control values.
Serum Parent = parent compound concentration as µg/mL of serum
Serum Bis = bisphenol concentration as µg/mL of serum
Serum Quin = diphenoquinone concentration as µg/g serum
Liver Parent = parent compound concentration as µg/g liver
Liver Bis = bisphenol concentration as µg/g liver
Liver Quin = diphenoquinone concentration as µg/g liver

EXAMPLE 26

Measurement of Antioxidant Activity and Bioavailability of Compounds of Formula (1) By In Vivo Screening in Male Sprague-Dawley Rats A. Experimental Protocol A typical experiment consists of 4–6 groups of rats (N=5 per group) with 1 group being a control which receives no MDL compound and the other groups being treated with 0.3% MDL compound. Some of the compounds are either repeated at 0.3% or evaluated again at the lower dose of 0.1%. House Male Sprague-Dawley rats, 50–100 g, (Harlan Laboratories, Indianapolis, Ind.) in groups of 5, feeding ad libitum water and Purina Rodent chow (#5002) with or without MDL compound as a dietary admixture for 4 days. Make dietary admixtures (0.3%) by mixing 1.2 grams of an MDL compound with 400 grams of Purina rodent chow (#5002). Mix the MDL compound with approximately 50 grams of food using a mortar and pestle. This is added to the remainder of the food and mixed for 3 hours on a rotary mixer. In the morning of day 5, anesthetize non-fasted rats with carbon dioxide, and collect blood by cardiac puncture. Sacrifice rats by cervical dislocation. Record body weights and liver weights in grams. Record food consumption as grams·day$^{-1}$·rat$^{-1}$. Deaths are recorded as mortality. Use aliquots of fresh serum for clinical chemistries, thiobarbituric acid reactive substances (TBARS) and conjugated diene measurements. Freeze aliquots of serum (~0.5 mL) and whole livers at −20° C. for compound and metabolite concentration determination at a later time.

B. Clinical Chemistries

Allow blood to clot at room temperature for 30 minutes. Obtain serum after centrifugation for 10 min at 4° C. at 3000 rpm in a Beckman J-6M/E centrifuge with a JS-4.2 rotor. Analyze fresh serum by a COBAS MIRA S autoanalyzer (Roche Diagnostics) using Roche diagnostic reagents for the following clinical chemistry measurements: alkaline phosphatase (ALP, kit # 44553), alanine transaminase (ALT, kit # 42375), aspartate aminotransferase (AST, kit # 42381), total cholesterol (CHOL, kit # 44334), triglyceride (TG, kit # 44120), and glucose (GLU, kit # 44558). Calculate ALP, ALT, and AST as units/L. Calculate cholesterol, triglycerides, and glucose as mg/dL.

C. HPLC—Quantitation of Compound of Metabolite Concentration in Serum and Liver

Determine serum and liver concentrations of parent compound and the metabolites, bisphenol and diphenoquinone, by reverse phase HPLC using a Waters 990 Powerline system. Homogenize livers (1 gram samples) with 5.0 mL PBS, pH 7.4, using a Polytron tissue homogenizer at setting 5 for 20–30 seconds. Extract serum or liver homogenates as follows: add 100 µL of either serum or homogenate to 2.0 mL diethyl ether:ethanol (3:1) while vortexing the tube. Cap the sample tubes and centrifuge for 10 min at 5° C. at 3500 rpm in a Beckman GPKR centrifuge with a GH 3.7 rotor. Transfer the supernatants to clean tubes and dry under $N_2$. Reconstitute samples with 200 µL of acetonitrile:hexane:0.1 M ammonium acetate (90:6.5:3.5, by vol.). Then, inject 100 µL onto a Waters Deltapak C18-300 Å column, and elute with an 83% acetonitrile:17% water mobile phase at a flow rate of 1.5 mL/min. Record absorbances at the wavelengths of 240, 254, and 420nm. Calculate compound concentrations from known quantities of authentic parent compounds after correction for recovery. Calculate concentrations as µg/mL. Calculate concentrations as µg/mL of serum and µg/g of liver.

D. Thiobarbituric Acid Reactive Substances (TBARS) Assay

In this assay the oxidation of serum lipids is initiated with $CuSO_4$, resulting in the formation of aldehydes, such as malondialdehyde (MDA). Upon incubation with thiobarbituric acid, the absorbance of the aldehydes can be detected at 530–540 nm. As stated in the previous example, TBARS values which are lower than control serum values indicate the relative ability of a test compound to inhibit the oxidation of lipids in a sample. Measure TBARS as follows: mix 100 µL of serum with 400 µL of a 5 mmol $CuSO_4$ solution and incubate at 37° C. for 3 hr. Stop the reactions by addition of 1.0 mL of 20% trichloroacetic acid. Then add 1.0 mL of 0.67% thiobarbituric acid in 0.05 N sodium hydroxide, mix, and incubate the samples for 30 min at 90° C. Centrifuge samples briefly to pellet undissolved material, and transfer the supernatants to a 96-well microtiter plate. Measure absorbances at 540 nm using a Biotek model EL311 microplate reader. The nmoles of MDA produced are calculated from a standard curve of 0 to 10 nmoles of MDA prepared from malonaldehyde bis(dimethylacetal). Serum samples from treated rats are compared to serum samples from control rats that received no MDL compound.

E. Conjugated Diene Determination

Conjugated diene lag phase is another indicator of the oxidation of lipids. Lipids exposed to $Cu^{++}$ form conjugated dienes that absorb ultraviolet light in the range of 230 to 235 nm. The lag phase of diene formation gives an indication of the amount of oxidation of the lipids. A lag phase longer than control samples indicate inhibition of the oxidation. Determine conjugated diene lay phase using a Varian DMS200 spectrophotometer (fitted with a constant temperature, 5 cuvette sample changer) at 30° C. Add twenty (20) µL of pooled serum to cuvettes containing 3.0 mL phosphate buffered saline, pH 7.5, and mix. Measure the absorbances of all cuvettes and set the instrument baseline to zero using the lowest absorbing sample. Next, add 100 µL of 1 mmol $CuSO_4$ and mix immediately. Record the absorbance of each cuvette at 2 min intervals for a period of 840 min. Capture the data and transfer to a Microsoft EXCEL® spreadsheet where the curves are smoothed and differentials obtained. Determine lag times mathematically as minutes. Pool serum samples (N=5); data presented are the mean values of 2 determinations. Compare serum samples from treated rats to serum samples from control rats that received no MDL compound.

Tables 5, 6 and 7 below present summary data from the individual experiments of this testing procedure. Table 5 presents measurements of the serum chemistries in the male Sprague-Dawley rats, Table 6 presents the animal parameters and Table 7 provides the drug or metabolite concentrations in both the serum and the liver.

TABLE 5

Antioxidant Effects of Compounds of Formula (1) in Male Sprague-Dawley Rats as a Percent of Control

| MDL No. | Diet % | ALP | AST | ALT | CHOL | GLUC | TRIG | TBARS | CONJ. DIENE (min.) |
|---|---|---|---|---|---|---|---|---|---|
| 103,294 | 0.3 | 124% | 88% | 132% | 102% | 103% | 56% | 18% | ND* |
| 103,649 | 0.3 | 74% | 82% | 119% | 89% | 101% | 143% | 29% | 375 |
| 103,714 | 0.3 | 111% | 104% | 120% | 90% | 95% | 122% | 21% | ND |
| 103,960 | 0.3 | 125% | 102% | 117% | 113% | 110% | 80% | 24% | 363 |
| 104,102 | 0.3 | 101% | 82% | 114% | 100% | 98% | 127% | 71% | 229 |
| 104,191 | 0.3 | 81% | 146% | 149% | 109% | 106% | 112% | 20% | 708 |
| 104,487 | 0.3 | 137% | 124% | 129% | 127% | 92% | 108% | 87% | ND |
| 104,535 | 0.3 | 151% | 94% | 108% | 103% | 112% | 60% | 11% | ND |
| 105,411 | 0.3 | 76% | 87% | 122% | 105% | 96% | 100% | 29% | 400 |
| 107,059 | 0.3 | 118% | 140% | 116% | 89% | 96% | 35% | 78% | 201 |

*ND = not determined
N = 5 rats per group
Diet % = (weight MDL compound/weight food) × (100)
Conj. Diene = conjugated diene lag phase in minutes (Mean of 2 determinations of pooled samples, N = 5)
The data in Table 5, except for conjugated dienes and diet percent, have been normalized as follows:
% Control = (Mean, treated group/Mean, control group) × (100)
ALP = alkaline phosphatase, U/mL
AST = aspartate aminotransferase, U/mL
ALT = alanine aminotransferase, U/mL
CHOL = total cholesterol, mg/dL
TG = triglycerides, mg/dL
GLU = glucose, mg/dL
TBARS = thiobarbituric acid reactive substances, expressed as nmoles MDA

TABLE 6

Animal Parameters as a Percent of Control

| MDL No. | Diet % | food | body wt. | lw/bw | mortality |
|---|---|---|---|---|---|
| 103,294 | 0.3 | 108% | 101% | 129% | 0% |
| 103,649 | 0.3 | 95% | 94% | 111% | 0% |
| 103,714 | 0.3 | 102% | 103% | 121% | 0% |
| 103,960 | 0.3 | 105% | 100% | 130% | 0% |
| 104,102 | 0.3 | 92% | 97% | 121% | 0% |
| 104,191 | 0.3 | 76% | 92% | 126% | 0% |
| 104,487 | 0.3 | 90% | 95% | 150% | 0% |
| 104,535 | 0.3 | 95% | 102% | 119% | 0% |
| 105,411 | 0.3 | 95% | 101% | 114% | 0% |
| 107,059 | 0.3 | 95% | 95% | 107% | 0% |

N = 5 rats/group
Diet % = (weight MDL compound/weight food) × (100)
The data in Table 6 have been normalized according to the formula presented in Table 5.
Food = grams eaten per day per rat
Body weight = weight in grams
LW/BW = (liver weight/body weight in grams)
Mortality = deaths per group

TABLE 7

Drug and Metabolite Concentration in Rat Serum and Liver

| | | Serum | | | Liver | | |
|---|---|---|---|---|---|---|---|
| MDL No. | Diet % | Parent | Bis | Quin | Parent | Bis | Quin |
| 103,294 | 0.3 | 21.7 | 0 | 0 | 64.6 | 0 | 0 |
| 103,649 | 0.3 | 1.4 | 0 | 0 | 0 | 0 | 0 |
| 103,714 | 0.3 | 2.7 | 0 | 0 | 0 | 0 | 0 |
| 103,960 | 0.3 | 8.7 | 0 | 0 | 47.3 | 39.4 | 0 |
| 104,102 | 0.3 | 32.8 | 0 | 0 | 481 | 0 | 0 |
| 104,191 | 0.3 | 6.9 | 0 | 0 | 16.1 | 0 | 0 |
| 104,487 | 0.3 | 4.1 | 0 | 0 | 3.8 | 11.5 | 0 |
| 104,535 | 0.3 | 16.3 | 0 | 0 | 60.3 | 0 | 0 |
| 105,411 | 0.3 | 1.1 | 0 | 0 | 0 | 0 | 0 |
| 107,059 | 0.3 | 0 | 0 | 0 | 0 | 0 | 0 |

The data in Table 7 are presented as Means (N = 5) and have not been normalized to control values.
Serum Parent = parent compound concentration as μg/mL of serum
Serum Bis = bisphenol concentration as μg/mL of serum
Serum Quin = diphenoquinone concentration as μg/g serum
Liver Parent = parent compound concentration as μg/g liver
Liver Bis = bisphenol concentration as μg/g liver
Liver Quin = diphenoquinone concentration as μg/g liver

EXAMPLE 27

Antiatherosclerotic Effects of Compounds of Formula (1) in Cholesterol-Fed Female New Zealand White Rabbits A. Experimental Protocol Conduct four independent experiments. Each experiment has a control group and 1–5 groups treated with MDL compound (N=5 per group). Feed Female New Zealand White Rabbits (Hazelton, ~2.0–2.3 kg) 1% cholesterol enriched rabbit chow (Purina # 5322) with or without 0.4% of an MDL compound. Solubilize the MDL compound in 100% ethanol, spray on the chow, and dry overnight in a chemical fume hood. Alternatively, the MDL compounds can be incorporated into the rabbit food by Purina. Control chow is sprayed with ethanol. Feed rabbits 100 grams food per day for 70 days and allow water to be made available ad libitum. Rabbits (fasted overnight) are bled (~2 mL) from a marginal ear vein periodically to monitor serum cholesterol levels. Euthanize rabbits on day 70 by carbon dioxide overdose. Record total body and liver weights in grams. Record food consumption as grams·day$^{-1}$. Use aliquots of fresh serum for clinical chemistries, lipoprotein cholesterol determination, thiobarbituric acid reactive substances (TBARS) and compound and metabolite concentrations is serum. Freeze livers (~5 gram aliquots) at −20° C. for compound and metabolite concentration determination at a later time.

Dissect aortas immediately after each rabbit is killed. Excise the aorta from the ascending arch to the iliac bifurcation after debridement of extraneous adipose tissue. Store aortas overnight in phosphate buffered saline, pH 7.4, at 4° C. until final debridement. Cut open aortas longitudinally and stain with Sudan IV. After staining, pin flat the aortas and quantitate the areas of sudanophilic lesions after capturing an image electronically.

B. Clinical Chemistries

Allow blood to clot at room temperature for 30 minutes. Obtain serum after centrifugation for 10 min at 5° C. at 3000 rpm in a Beckman GPKR centrifuge with a GH 3.7 rotor. Analyze fresh serum by a COBA MIRA S autoanalyzer (Roche Diagnostics) using Roche diagnostic reagents for total cholesterol (CHOL, kit # 44334) and triglyceride (TG, kit # 44120). Calculate cholesterol and triglycerides as mg/dL.

C. TBARS Assay

Initiate the oxidation of serum lipids with $CuSO_4$ to form aldehydes, such as malondialdehyde (MDA). Upon incubation with thiobarbituric acid, detect the absorbance of the aldehydes at 530–540 nm. Measure TBARS as follows: mix 50 μL of serum with 50 μL of 0.9% saline and 400 μL of a 5 mmol $CuSO_4$ solution and incubate at 37° C. for 5 hr. Stop the reactions by addition of 1.0 mL of 20% trichloroacetic acid. Add 1.0 mL of 0.67% thiobarbituric acid in 0.05 N sodium hydroxide, mix and incubate the samples for 30 min at 90° C. Centrifuge the samples briefly to pellet undissolved material and transfer the supernatants to a 96-well microtiter plate. Measure absorbances at 540 nm using a Biotek model EL311 microplate reader. The nmoles of MDA produced are calculated form a standard curve of 0 to 10 nmoles of MDA prepared form malonaldehyde bis(dimethyacetal). Compare serum samples from treated rabbits to serum samples from control rabbits that received no MDL compound.

D. HPLC—Quantitation of Serum and Liver Compound and Metabolite Concentration

Determine the serum and liver concentrations of parent compounds and the metabolites, bisphenol and diphenoquinone, by reverse phase HPLC using a Waters 990 Powerline system. Homogenize livers (1 gram) with 5.0 mL PBS, pH 7.4, using a Polytron tissue homogenizer at setting 5 for 20–30 seconds. Extract serum or liver homogenates as follows: Add 100 μL of either serum or homogenate to 2.0 mL diethyl ether:ethanol (3:1) while vortexing the tube. Cap and centrifuge the sample tubes for 10 min at 5° C. at 3500 rpm in a Beckman GPKR centrifuge with a GH 3.7 rotor. Transfer the supernatants to clean tubes and dry under $N_2$. Reconstitute samples with 200 μL of acetonitrile:hexane:0.1 ammonium acetate (90:6.5:3.5, by vol.). Then, inject 100 μL onto a Waters Deltapak C18-300 Å column, and elute with an 83% acetonitrile:17% water mobile phase at a flow rate of 1.5 mL/min. Record absorbances at the wavelengths of 240, 254, and 420 nm. Calculate compound concentrations from known quantities of authentic parent compounds after correction for recovery. Calculate concentrations as μg/mL or serum and μg/g of liver.

E. HPLC—Separation and Quantitation of Lipoprotein Subfraction Cholesterol Levels Separate lipoprotein fractions of VLDL, LDL and HDL on a Sepharose 6HR column (1×30 cm, Pharmacia) attached to a Waters Powerline HPLC system. Inject 50 μL of serum onto the column and elute with phosphate buffered saline, pH 7.4, at a flow rate of 0.5 mL/min. Add cholesterol reagent (Roche Diagnostics, kit # 44334, diluted with 20 mL of water and then 20 mL of 0.9% saline) at 0.2 mL/min to the post column eluant and incubate in knitted PFTE Kratos reaction coil (Applied Biosystems) at 37° C. for 5 min. Measure absorbance at 500 nm. Quantitate the lipoprotein subfractions as follows:

(total serum cholesterol)×(% area under the curve for each subfraction).

In addition, the compounds of formula (1) can be used as chemical antioxidant additives in organic materials normally subject to oxidative deterioration, such as, for example, rubber, plastics, fats, petroleum products and the like. In general, a preservative amount of a compound of formula (1), which is sufficient in concentration to inhibit oxidative deterioration of the material to be protected, is admixed with the material subject to oxidation. The preservative amount of a compound of formula (1) will generally vary from about 0.01% to about 1.0% by weight.

What is claimed is:

1. A compound of the formula

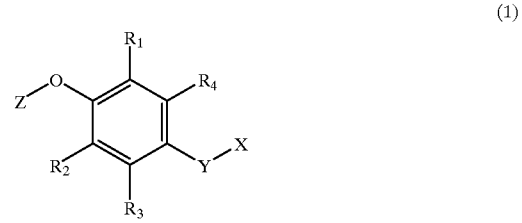

wherein

X is selected from the group consisting of

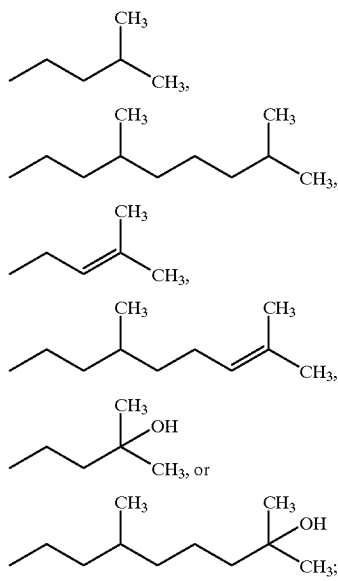

Y is thio, oxy or a methylene group;

Z is hydrogen or —C(O)—$(CH_2)_m$—Q wherein Q is hydrogen or —COOH and m is an integer 1, 2, 3 or 4;

$R_1$ is $C_1$–$C_6$ alkyl; and $R_2$, $R_3$ and $R_4$ are each independently hydrogen or $C_1$–$C_6$ alkyl;

or a stereoisomer thereof.

2. A compound of claim 1 wherein $R_1$ is methyl or tertiarybutyl; $R_2$ and $R_3$ are each independently hydrogen, methyl or tertiarybutyl; $R_4$ is hydrogen or methyl; and Z is hydrogen, acetyl or succinyl.

3. A compound of claim 1 wherein X is selected from the group consisting of

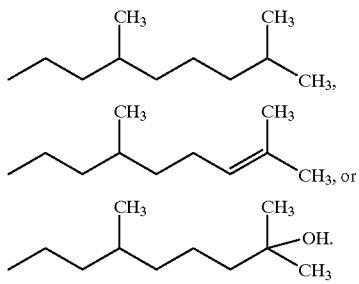

4. A compound of claim 3 wherein Z is hydrogen, acetyl or succinyl; $R_1$ is methyl or tertiarybutyl; $R_2$ and $R_3$ are each independently hydrogen, methyl or tertiarybutyl; $R_4$ is hydrogen or methyl.

5. A compound of claim 4 wherein Z is hydrogen.

6. A compound of claim 1 wherein Z is —C(O)—(CH$_2$)$_m$—Q wherein Q is hydrogen or —COOH and m is an integer 1, 2, 3 or 4.

7. A compound of claim 6 wherein $R_1$ is methyl or tertiarybutyl; $R_2$ and $R_3$ are each independently hydrogen, methyl or tertiarybutyl; and $R_4$ is hydrogen or methyl.

8. A compound according to claim 2 wherein Z is thio.

9. A compound according to claim 2 wherein Z is oxy.

10. A compound of claim 1 wherein the compound is Phenol, 2,6-bis(1,1-dimethylethyl)-4-[(3,7-dimethyl-6-octenyl)oxy]-, (S)-.

11. A compound of claim 1 wherein the compound is Phenol, 2-(1,1-dimethylethyl)-4-[(3,7-dimethyl-6-octenyl)oxy]-, (S)-.

12. A compound of claim 1 wherein the compound is Phenol, 2-(1,1-dimethylethyl)-4-[(3,7-dimethyl-6-octenyl)thio]-, (S)-.

13. A compound of claim 1 wherein the compound Phenol, 2,6-bis(1,1-dimethylethyl)-4-[(3,7-dimethyl-6-octenyl)thio]-.

14. A compound of claim 1 wherein the compound is Phenol, 2,6-bis(1,1-dimethylethyl)-4-[(3,7-dimethyloctyl)oxy]-.

15. A compound of claim 1 wherein the compound is Phenol, 2-(1,1-dimethylethyl)-4-[(3,7-dimethyloctyl)thio]-.

16. A compound of claim 1 wherein the compound is Phenol, 2,6-bis(1,1-dimethylethyl)-4-[(7-hydroxy-3,7-dimethyloctyl)thio]-.

17. A compound of claim 1 wherein the compound Phenol, 2,6-bis(1,1-dimethylethyl)-4-[(3,7-dimethyl-6-octenyl)oxy]-, (R)-.

18. A compound of claim 1 wherein the compound is Phenol, 2-(1,1-dimethylethyl)-4-[(3,7-dimethyl-6-octenyl)oxy]-.

19. A compound of claim 1 wherein the compound is Phenol, 2,5-bis(1,1-dimethylethyl)-4-[(3,7-dimethyl-6-octenyl)oxy]-, (S)-.

20. A method comprising administering to a patient having need thereof, a compound useful for the treatment of atherosclerosis and chronic inflammatory disorders; for inhibiting cytokine-induced expression of VCAM-1 and/or ICAM-1; for inhibiting the peroxidation of LDL lipid; and for lowering plasma cholesterol; said compound having the formula

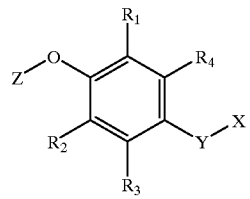

wherein

X is selected from the group consisting of

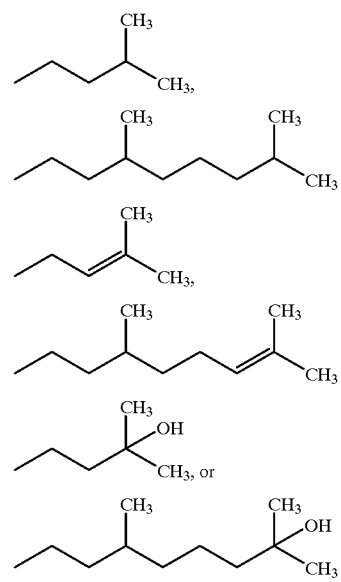

Y is thio, oxy or a methylene group;

Z is hydrogen or —C(O)—(CH$_2$)$_m$—Q wherein Q is hydrogen or —COOH and m is an integer 1, 2, 3 or 4;

$R_1$ is $C_1$–$C_6$ alkyl; and $R_2$, $R_3$ and $R_4$ are each independently hydrogen or $C_1$–$C_6$ alkyl;

or a stereoisomer thereof.

21. A method of inhibiting the progression of atherosclerosis in a patient in need thereof comprising administering to the patient an effective anti-atherosclerotic amount of a compound of claim 20.

22. A method of treating a patient for atherosclerosis comprising administering to the patient an effective antiatherosclerotic amount of a compound of claim 20.

23. A method of inhibiting peroxidation of LDL cholesterol in a patient in need thereof comprising administering to the patient an effective antioxidant amount of a compound of claim 20.

24. A method of lowering plasma cholesterol level in a patient in need thereof comprising administering to the patient a plasma cholesterol lowering amount of a compound of claim 20.

25. A method of inhibiting cytokine-induced expression of vascular cell adhesion molecule-1 and/or intercellular adhesion molecule-1 in a patient in need thereof comprising administering to the patient an effective vascular cell adhesion molecule-1 and/or intercellular adhesion molecule-1 inhibiting amount of a compound of claim 20.

26. A method of treating a patient afflicted with a chronic inflammatory disease comprising administering to the patient a therapeutically effective amount of a compound of claim 20.

27. A method according to claim 26 wherein the inflammatory disease is asthma.

28. A method according to claim 26 wherein the inflammatory disease is chronic inflammation.

29. A method according to claim 26 wherein the inflammatory disease is rheumatoid arthritis.

30. A method according to claim 26 wherein the inflammatory disease is autoimmune diabetes.

31. A method according to claim 26 wherein the inflammatory disease is transplant rejection.

32. A method according to claim 26 wherein the inflammatory disease is tumor angiogenesis.

* * * * *